(12) United States Patent
Kousoulas

(10) Patent No.: US 10,130,703 B2
(45) Date of Patent: Nov. 20, 2018

(54) VACCINES AGAINST GENITAL HERPES SIMPLEX INFECTIONS

(71) Applicant: Board of Supervisors of Louisiana State University and Agricultural and Mechanical College, Baton Rouge, LA (US)

(72) Inventor: Konstantin G. Kousoulas, Baton Rouge, LA (US)

(73) Assignee: BOARD OF SUPERVISORS OF LOUISIANA STATE UNIVERSITY AND AGRICULTURAL AND MECHANICAL COLLEGE, Baton Rouge, LA (US)

( * ) Notice: Subject to any disclaimer, the term of this patent is extended or adjusted under 35 U.S.C. 154(b) by 0 days.

(21) Appl. No.: 15/310,004

(22) PCT Filed: May 8, 2015

(86) PCT No.: PCT/US2015/029905
§ 371 (c)(1),
(2) Date: Nov. 9, 2016

(87) PCT Pub. No.: WO2015/172033
PCT Pub. Date: Nov. 12, 2015

(65) Prior Publication Data
US 2017/0266275 A1 Sep. 21, 2017

Related U.S. Application Data

(60) Provisional application No. 61/990,975, filed on May 9, 2014.

(51) Int. Cl.
*A61K 39/245* (2006.01)
*C12N 7/00* (2006.01)
*A61K 39/00* (2006.01)

(52) U.S. Cl.
CPC .............. *A61K 39/245* (2013.01); *C12N 7/00* (2013.01); *A61K 2039/5254* (2013.01); *C12N 2710/16634* (2013.01)

(58) Field of Classification Search
None
See application file for complete search history.

(56) References Cited

U.S. PATENT DOCUMENTS
7,374,768 B1 5/2008 Inglis

FOREIGN PATENT DOCUMENTS

| WO | WO9213943 A1 | 8/1992 |
| WO | WO9936087 A1 | 7/1999 |
| WO | WO2008141151 A2 | 11/2008 |
| WO | WO2013177172 A2 | 11/2013 |

OTHER PUBLICATIONS

Foster et al. Functional and physical interactions of the herpes simplex virus type 1 UL20 membrane protein with glycoprotein K. J Virol. Jul. 2008;82(13):6310-23. Epub Apr. 23, 2008.*
Mori et al. HF10, an attenuated herpes simplex virus (HSV) type 1 clone, lacks neuroinvasiveness and protects mice against lethal challenge with HSV types 1 and 2. Microbes and Infection 7 (2005) 1492-1500.*
Ushijima et al. Determination and analysis of the DNA sequence of highly attenuated herpes simplex virus type 1 mutant HF10, a potential oncolytic virus. Microbes and Infection 9 (2007) 142e149.*
Iyer, et al.: "Single dose of glycoprotein K (gK)-deleted HSV-1 live-attenuated virus protects mice against lethal vaginal challenge with HSV-1 and HSV-2 and induces lasting T cell memory immune responses." Virol J. 2013, 10:317; Abstract, p. 3, Fig 1 and its legend; p. 8, col. 1.
Saied, et al.: "A replication competent HSV-1 (McKrae) with a mutation in the amino-terminus of glycoprotein K (gK) is unable to infect mouse trigeminal ganglia after cornea infection." Current Eye Research, Informa Healthcare USA, vol. 39, No. 6, pp. 596-603, Jan. 1, 2014.
Charles, et al.: "Phenylalanine residues at the carboxyl terminus of the herpes simplex virus 1 UL20 membrane protein regulate cytoplasmic virion envelopment and infectious virus production." J Virol. Epub, Apr. 23, 2014 88(13):7618-27; Abstract, p. 7619, col. 1; p. 7622, col. 2, 1st para, and Fig 5 and its legend.
Stanfield, et al.: "A single intramuscular vaccination of mice with the HSV-1 VC2 virus with mutations in the glycoprotein K and the membrane protein UL20 confers full protection against lethal intravaginal challenge with virulent HSV-1 and HSV-2 strains." PLoS One, Oct. 28, 2014, 9(10):e109890; in entirety.
Stanfield, et al.: "Vaccination with the HSV-1 Attentuated Virus VC2 Protects Mice against Lethal Challenge with Virulen HSV-1 and HSV-2 Strains (ID09)" 2013 Proc. Southeast Regional IDeA Meeting, p. 51, Nov. 17, 2013.
Jambunathan, et al.: "Site-Specific Proteolytic Cleavage of the Amino Terminus of Herpes Simplex Virus Glycoprotein K on Virion Particles Inhibits Virus Entry" Journal of Virology, vol. 85, No. 24, pp. 12910-12918, Dec. 15, 2011.
Foster, et al.: "Functional and Physical Interactions of the Herpes Simplex Virus Type 1 UL20 Membrane Protein with Glycoprotein K" Journal of Virology, The American Society for Microbiology, vol. 82, No. 13, pp. 6310-6323, Jul. 1, 2008.
International Search Report and Written Opinion for PCT/US15/029905, ISA//US, dated Aug. 10, 2015.

(Continued)

*Primary Examiner* — Nianxiang Zou
(74) *Attorney, Agent, or Firm* — David M. Saravitz; Williams Mullen, P.C.

(57) ABSTRACT

The present invention provides vaccines for treating or preventing a herpes simplex virus infection and methods of using and making the vaccine. Further provided are recombinant herpes simplex virus genomes, recombinant viruses, and immunogenic compositions.

13 Claims, 13 Drawing Sheets
Specification includes a Sequence Listing.

(56) References Cited

OTHER PUBLICATIONS

Supplementary European Search Report for EP 15789628, EPO, dated Sep. 26, 2017.
Melancon, et al., Genetic Analysis of the Herpes Simplex Virus Type 1 UL20 Protein Domains Involved in Cytoplasmic Virion Envelopment and Virus-Induced Cell Fusion, Journal of Virology, vol. 78, No. 14, pp. 7329-7343, Jul. 2004.

* cited by examiner

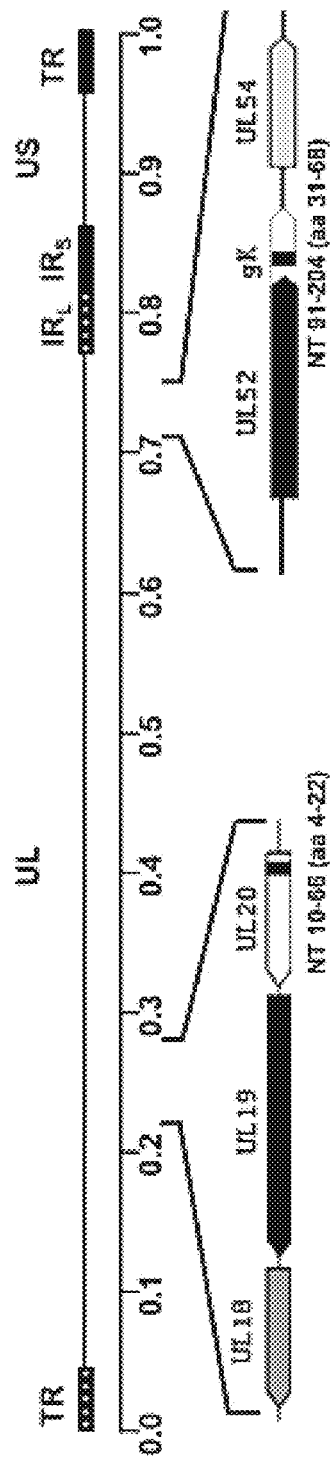
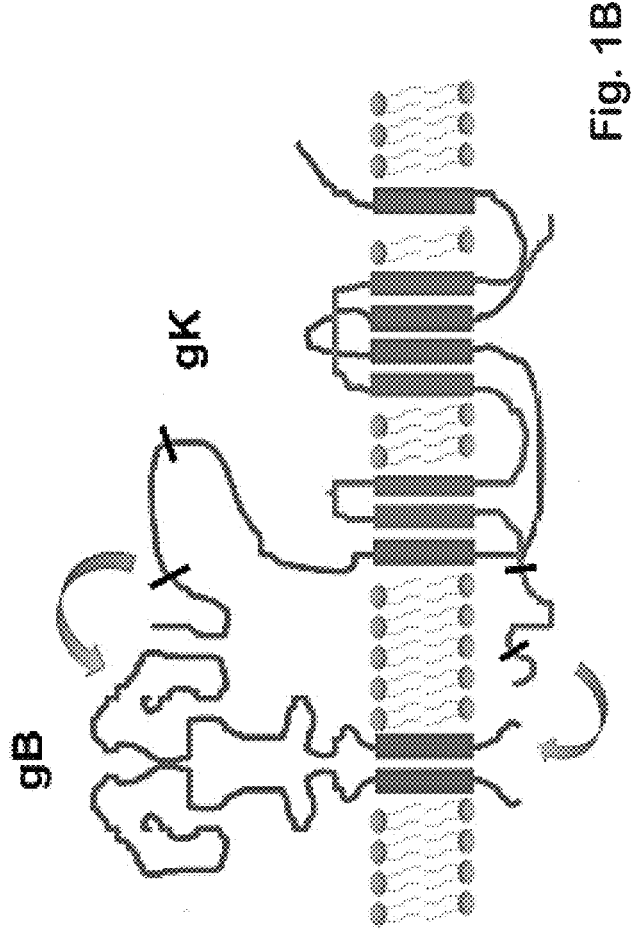
Fig. 1A
Fig. 1B

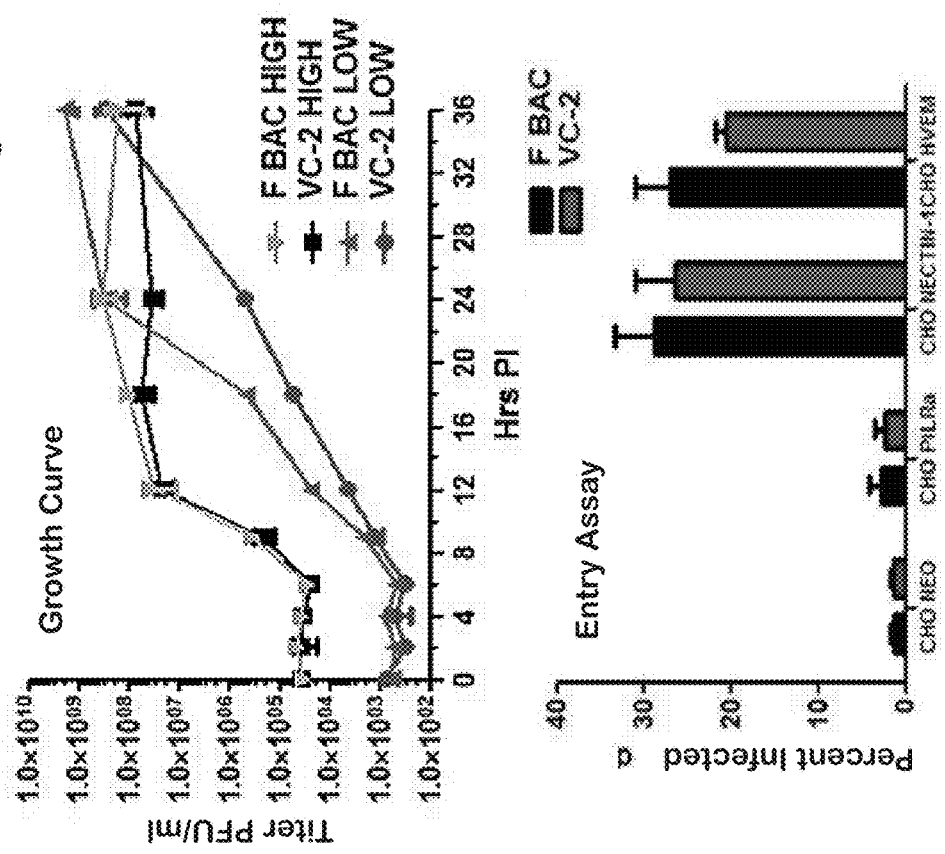
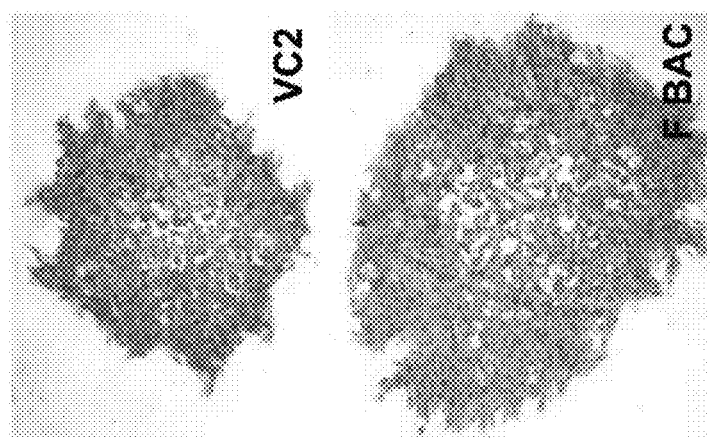
Fig. 2A, Fig. 2B, Fig. 2C

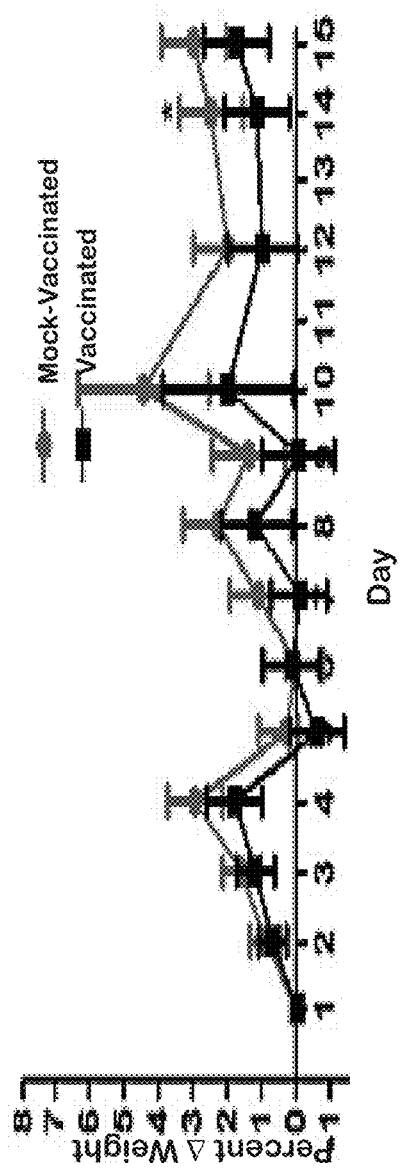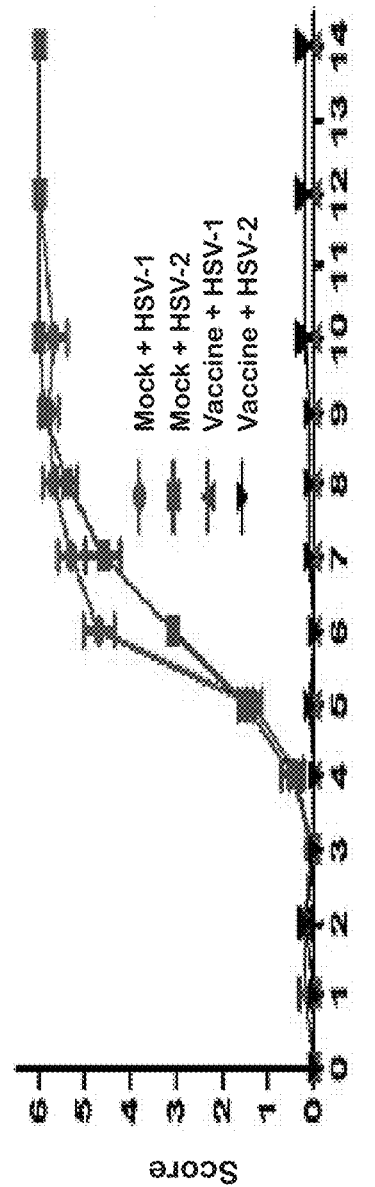
Fig. 3A
Fig. 3B

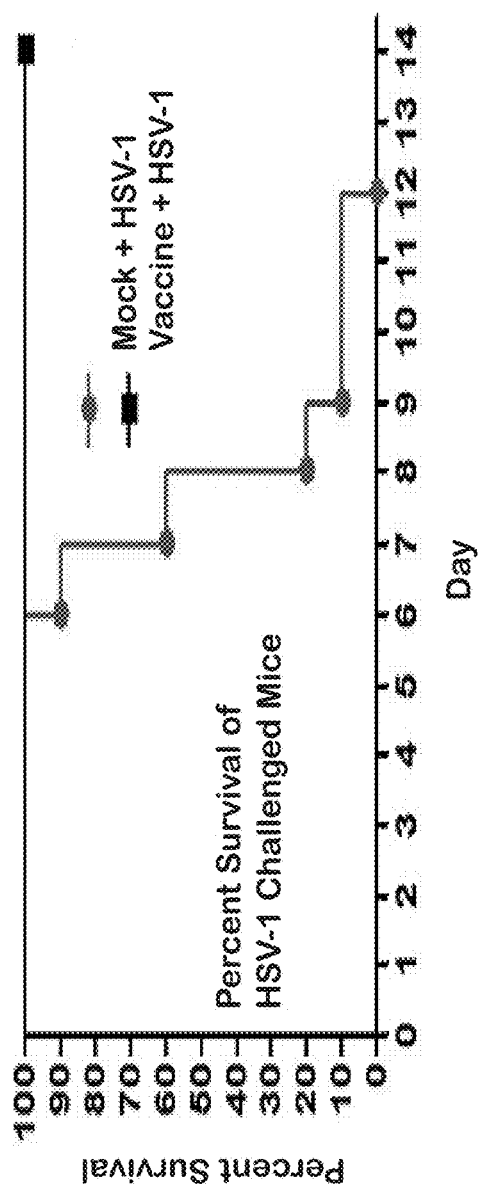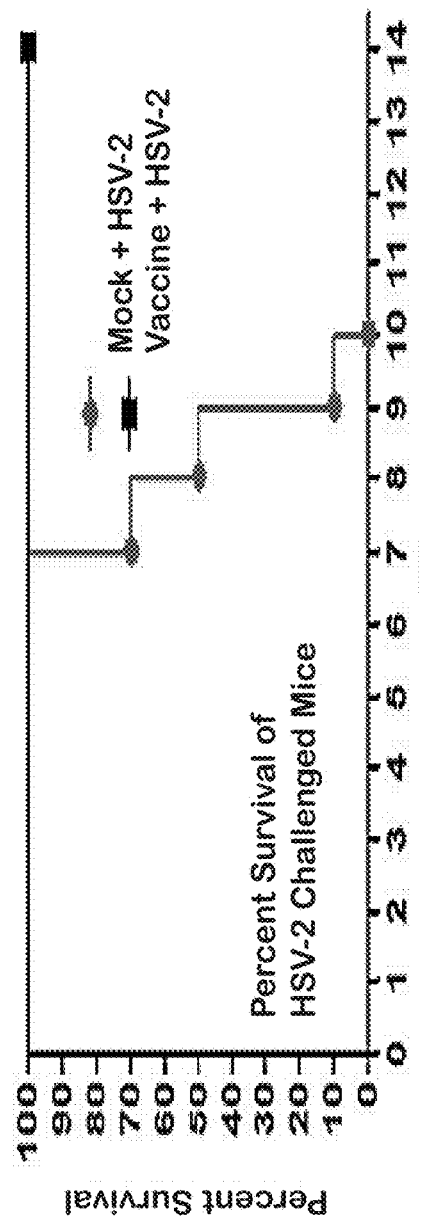

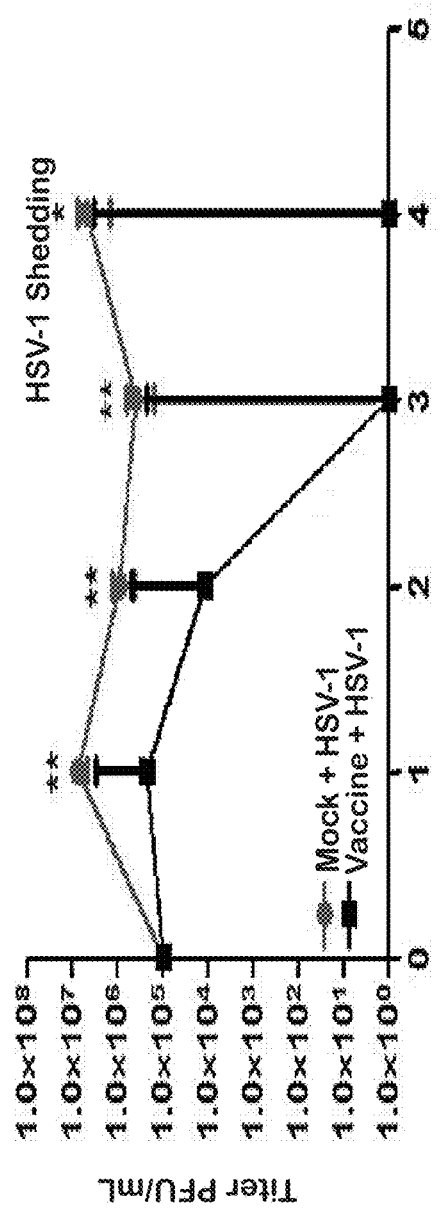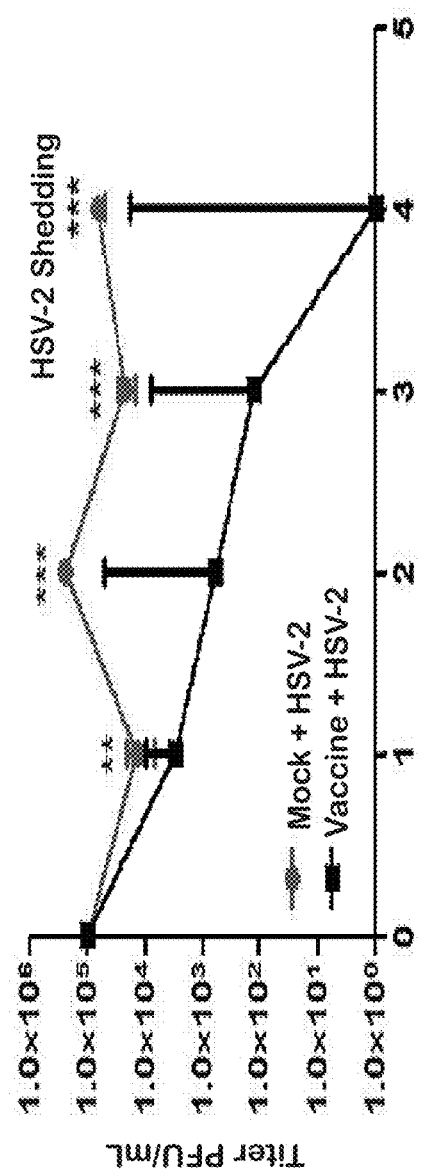

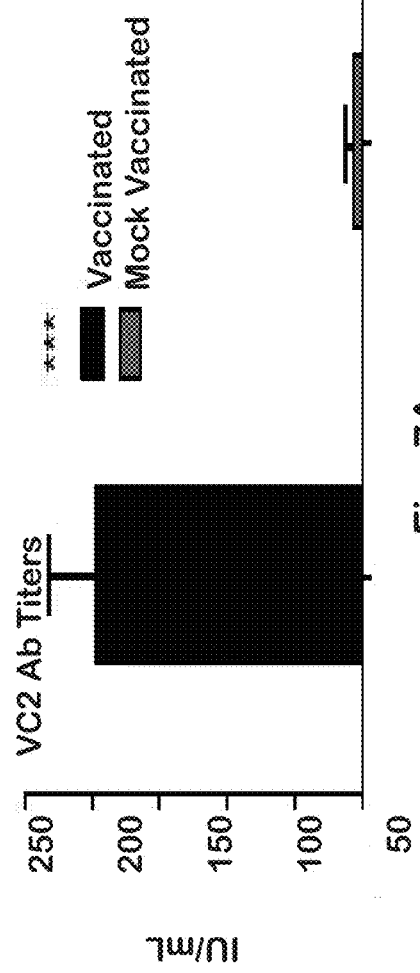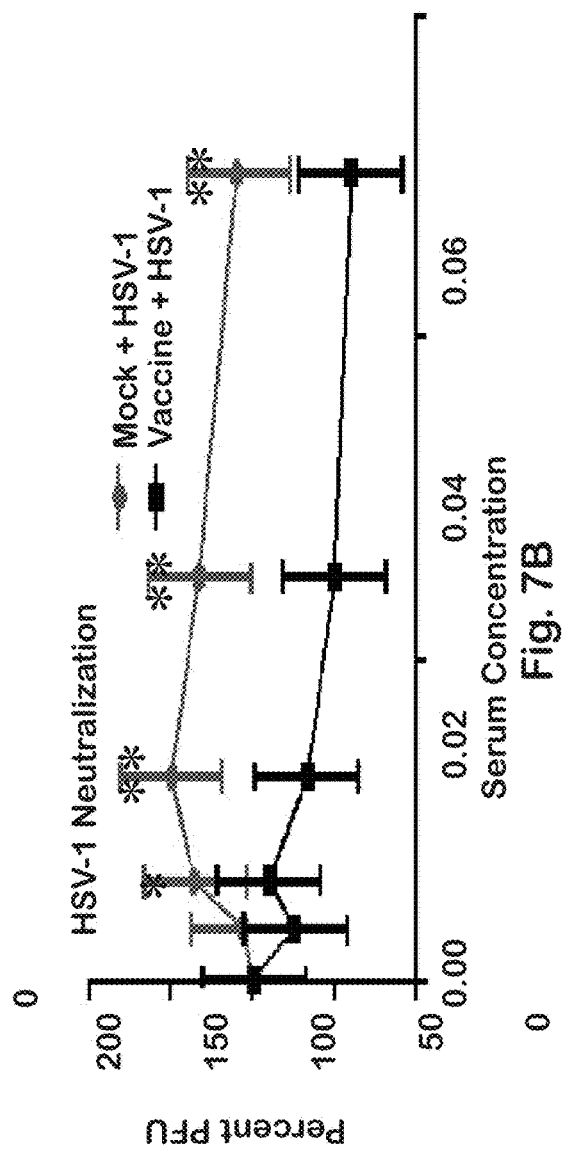
Fig. 7A
Fig. 7B

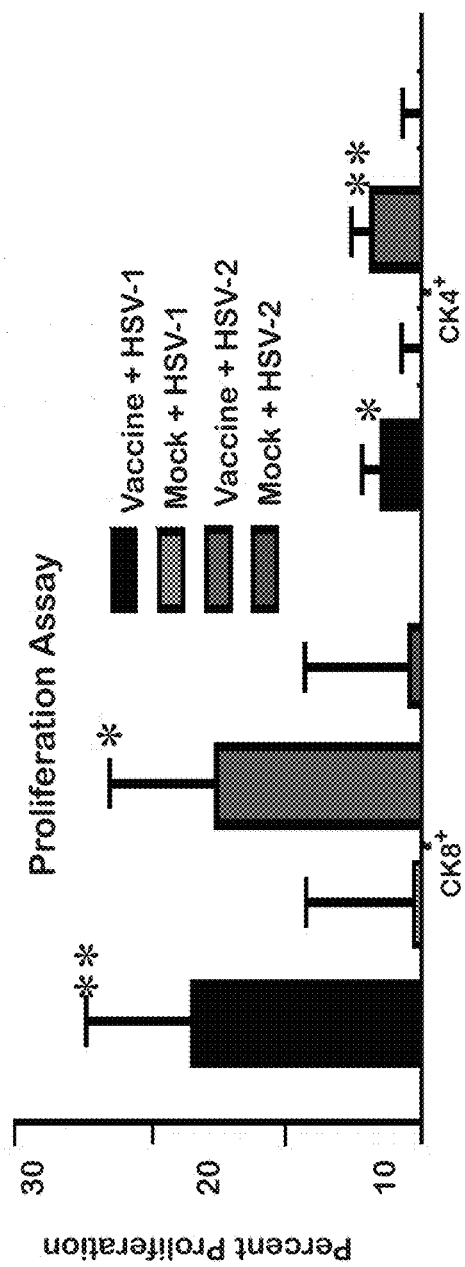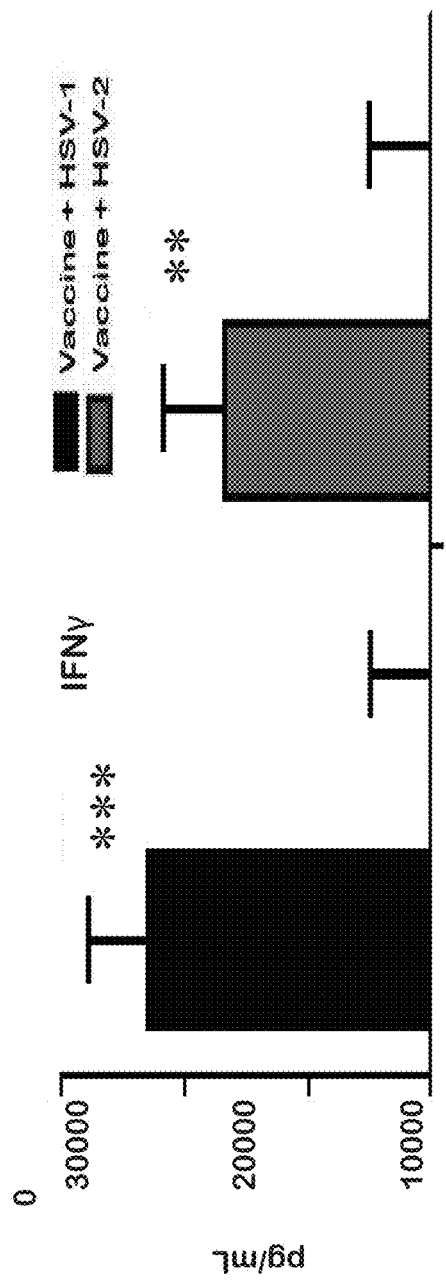

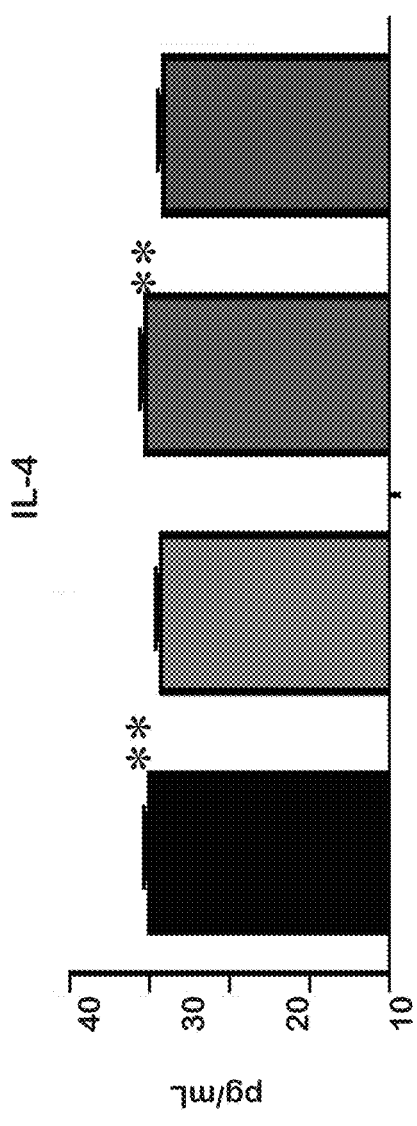
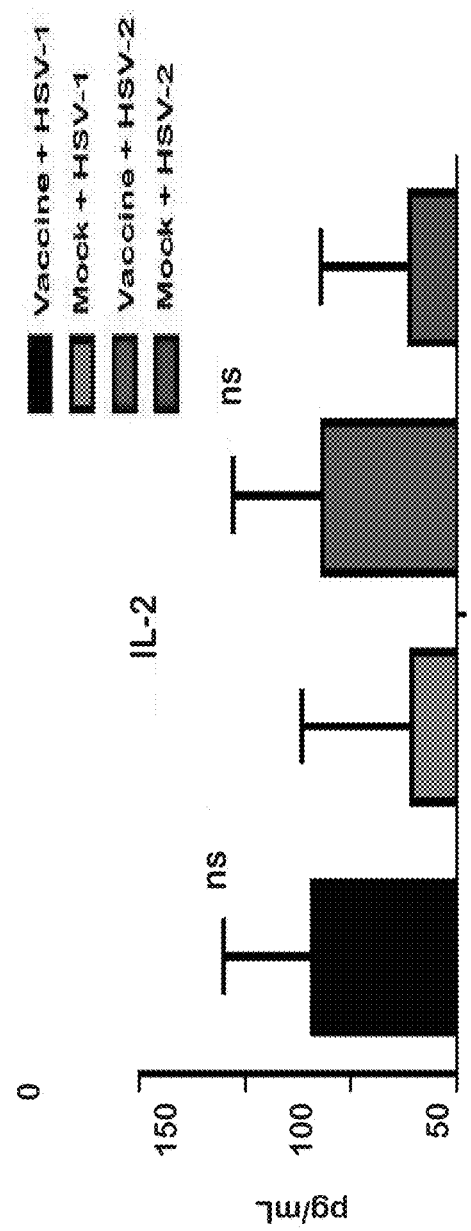

SEQUENCE LISTING

<160> NUMBER OF SEQ ID NOS: 25

<210> SEQ ID NO 1
<211> LENGTH: 669
<212> TYPE: DNA
<213> ORGANISM: Herpes Simplex Virus 1, strain F

<400> SEQUENCE: 1

```
atgaccatgc gggatgacct tcctctggtg gatcgagatc tggtcgacga ggccgccttc      60
gggggggagg agggagaact gccgctggag gaacagtttt cattgtcctc gtacggcacc     120
tctgattttt ttgtcagttc ggcatactcg cgtcttccgc cccatacccca gccggtcttt     180 tcaaagcgcg tgattctgtt cctttggtcg ttttggtcc tgaagccgtt ggagatggtg      240
gcagcgggca tgtattacgg gctgaccgga agggtggtgg cgccggcctg tatcctggcc     300
gccatcgtcg gctactacgt tacgtgggcg gtgcgggcgc tcctcctgta cgttaacatc     360
aagagggatc gtctgccgtt gtcggcgccc gtgttttggg ggatgtccgt gttttttggga     420 ggcacggccc tgtgtgcctt gttcgccgcc gcccacgaga ccttcagtcc ggacgggctt     480
ttccacttta tcgccaccaa ccaaatgctg ccacccaccg atccctgcg cacacgggcc     540 ctggggatag cctgtgcggc cggggcctcg atgtgggtgg cggcggcgga cagctttgcc     600
gcctctgcca atttcttcct ggcacgcttt tggaccaggg ccatcttgaa tgcacccgtc     660
gcgttctaa                                                              669
```

<210> SEQ ID NO 2
<211> LENGTH: 222
<212> TYPE: PRT
<213> ORGANISM: Herpes Simplex Virus 1, strain F

<400> SEQUENCE: 2

```
Met Thr Met Arg Asp Asp Leu Pro Leu Val Asp Arg Asp Leu Val Asp
1               5                   10                  15

Glu Ala Ala Phe Gly Gly Glu Glu Gly Glu Leu Pro Leu Glu Glu Gln
            20                  25                  30

Phe Ser Leu Ser Ser Tyr Gly Thr Ser Asp Phe Phe Val Ser Ser Ala
        35                  40                  45

Tyr Ser Arg Leu Pro Pro His Thr Gln Pro Val Phe Ser Lys Arg Val
    50                  55                  60

Ile Leu Phe Leu Trp Ser Phe Leu Val Leu Lys Pro Leu Glu Met Val
65                  70                  75                  80

Ala Ala Gly Met Tyr Tyr Gly Leu Thr Gly Arg Val Val Ala Pro Ala
                85                  90                  95

Cys Ile Leu Ala Ala Ile Val Gly Tyr Tyr Val Thr Trp Ala Val Arg
            100                 105                 110
```

```
Ala Leu Leu Leu Tyr Val Asn Ile Lys Arg Asp Arg Leu Pro Leu Ser
            115                 120                 125

Ala Pro Val Phe Trp Gly Met Ser Val Phe Leu Gly Gly Thr Ala Leu
        130                 135                 140

Cys Ala Leu Phe Ala Ala His Glu Thr Phe Ser Pro Asp Gly Leu
145                 150                 155                 160

Phe His Phe Ile Ala Thr Asn Gln Met Leu Pro Pro Thr Asp Pro Leu
                165                 170                 175

Arg Thr Arg Ala Leu Gly Ile Ala Cys Ala Ala Gly Ala Ser Met Trp
            180                 185                 190

Val Ala Ala Asp Ser Phe Ala Ala Ser Ala Asn Phe Phe Leu Ala
        195                 200                 205

Arg Phe Trp Thr Arg Ala Ile Leu Asn Ala Pro Val Ala Phe
    210                 215                 220
```

<210> SEQ ID NO 3
<211> LENGTH: 1017
<212> TYPE: DNA
<213> ORGANISM: Herpes Simplex Virus 1, strain F

<400> SEQUENCE: 3

```
atgctcgccg tccgttccct gcagcacctc tcaaccgtcg tcttgataac ggcgtacggc      60
ctcgtgctcg tgtggtacac cgtcttcggt gccagtccgc tgcaccgatg tatttacgcg     120
gtacgcccca ccggcaccaa caacgacacc gccctcgtgt ggatgaaaat gaaccagacc     180
ctattgtttc tgggggcccc gacgcacccc ccaacggggg ctggcgcaa ccacgcccat     240
atctgctacg ccaatcttat cgcgggtagg gtcgtgccct tccaggtccc acccgacgcc     300
atgaatcgtc ggatcatgaa cgtccacgag gcagttaact gtctggagac ctatggtac     360
acacgggtgc gtctggtggt cgtagggtgg ttcctgtatc tggcgttcgt cgccctccac     420
caacgccgat gtatgtttgg tgtcgtgagt cccgcccaca agatggtggc cccggccacc     480
tacctcttga actacgcagg ccgcatcgta tcgagcgtgt tcctgcagta cccctacacg     540
aaaattaccc gcctgctctg cgagctgtcg gtccagcggc aaaacctggt tcagttgttt     600
gagacggacc cggtcacctt cttgtaccac cgccccgcca tcgggtcat cgtaggctgc     660
gagttgatgc tacgctttgt ggccgtgggt ctcatcgtcg gcaccgcttt catatcccgg     720
ggggcatgtg caatcacata ccccctgttt ctgaccatca ccacctggtg ttttgtctcc     780
accatcggcc tgacagagct gtattgtatt ctgcggcggg gccggccccc aagaacgca     840
gacaaggccg ccgcccccggg gcgatccaag gggctgtcgg gcgtctgcgg gcgctgctgt     900
tccatcatcc tctcgggcat cgcagtgcga ttgtgttata tcgccgtggt ggccggggtg     960
gtgctcgtgg cgcttcacta cgagcaggag atccagaggc gcctgtttga tgtatga      1017
```

<210> SEQ ID NO 4
<211> LENGTH: 338
<212> TYPE: PRT
<213> ORGANISM: Herpes Simplex Virus 1, strain F

<400> SEQUENCE: 4

```
Met Leu Ala Val Arg Ser Leu Gln His Leu Ser Thr Val Val Leu Ile
1               5                  10                  15

Thr Ala Tyr Gly Leu Val Leu Val Trp Tyr Thr Val Phe Gly Ala Ser
            20                  25                  30

Pro Leu His Arg Cys Ile Tyr Ala Val Arg Pro Thr Gly Thr Asn Asn
        35                  40                  45
```

```
Asp Thr Ala Leu Val Trp Met Lys Met Asn Gln Thr Leu Leu Phe Leu
         50                  55                  60

Gly Ala Pro Thr His Pro Pro Asn Gly Gly Trp Arg Asn His Ala His
 65                  70                  75                  80

Ile Cys Tyr Ala Asn Leu Ile Ala Gly Arg Val Val Pro Phe Gln Val
                 85                  90                  95

Pro Pro Asp Ala Met Asn Arg Arg Ile Met Asn Val His Glu Ala Val
                100                 105                 110

Asn Cys Leu Glu Thr Leu Trp Tyr Thr Arg Val Arg Leu Val Val Val
                115                 120                 125

Gly Trp Phe Leu Tyr Leu Ala Phe Val Ala Leu His Gln Arg Arg Cys
130                 135                 140

Met Phe Gly Val Val Ser Pro Ala His Lys Met Val Ala Pro Ala Thr
145                 150                 155                 160

Tyr Leu Leu Asn Tyr Ala Gly Arg Ile Val Ser Ser Val Phe Leu Gln
                165                 170                 175

Tyr Pro Tyr Thr Lys Ile Thr Arg Leu Leu Cys Glu Leu Ser Val Gln
                180                 185                 190

Arg Gln Asn Leu Val Gln Leu Phe Glu Thr Asp Pro Val Thr Phe Leu
                195                 200                 205

Tyr His Arg Pro Ala Ile Gly Val Ile Val Gly Cys Glu Leu Met Leu
210                 215                 220

Arg Phe Val Ala Val Gly Leu Ile Val Gly Thr Ala Phe Ile Ser Arg
225                 230                 235                 240

Gly Ala Cys Ala Ile Thr Tyr Pro Leu Phe Leu Thr Ile Thr Thr Trp
                245                 250                 255

Cys Phe Val Ser Thr Ile Gly Leu Thr Glu Leu Tyr Cys Ile Leu Arg
                260                 265                 270

Arg Gly Pro Ala Pro Lys Asn Ala Asp Lys Ala Ala Ala Pro Gly Arg
                275                 280                 285

Ser Lys Gly Leu Ser Gly Val Cys Gly Arg Cys Cys Ser Ile Ile Leu
                290                 295                 300

Ser Gly Ile Ala Val Arg Leu Cys Tyr Ile Ala Val Ala Gly Val
305                 310                 315                 320

Val Leu Val Ala Leu His Tyr Glu Gln Glu Ile Gln Arg Arg Leu Phe
                325                 330                 335

Asp Val

<210> SEQ ID NO 5
<211> LENGTH: 612
<212> TYPE: DNA
<213> ORGANISM: Artificial Sequence
<220> FEATURE:
<223> OTHER INFORMATION: Synthetic sequence derived from HSV-1(F)

<400> SEQUENCE: 5
atgaccatgg aggagggaga actgccgctg gaggaacagt tttcattgtc ctcgtacggc      60
acctctgatt ttttgtcag ttcggcatac tcgcgtcttc cgccccatac ccagccggtc     120
ttttcaaagc gcgtgattct gttcctttgg tcgttttgg tcctgaagcc gttggagatg     180
gtggcagcgg gcatgtatta cgggctgacc ggaagggtgg tggcgccggc ctgtatcctg     240
gccgccatcg tcggctacta cgttacgtgg gcggtgcggg cgctcctcct gtacgttaac     300
atcaagaggg atcgtctgcc gttgtcggcg cccgtgtttt gggggatgtc cgtgtttttg     360
```

```
ggaggcacgg ccctgtgtgc cttgttcgcc gccgcccacg agaccttcag tccggacggg    420
cttttccact ttatcgccac caaccaaatg ctgccaccca ccgatcccct gcgcacacgg    480
gccctgggga tagcctgtgc ggccggggcc tcgatgtggg tggcggcggc ggacagcttt    540
gccgcctctg ccaatttctt cctggcacgc ttttggacca gggccatctt gaatgcaccc    600
gtcgcgttct aa                                                        612
```

<210> SEQ ID NO 6
<211> LENGTH: 203
<212> TYPE: PRT
<213> ORGANISM: Artificial Sequence
<220> FEATURE:
<223> OTHER INFORMATION: Synthetic sequence derived from HSV-1(F)

<400> SEQUENCE: 6

```
Met Thr Met Glu Glu Gly Glu Leu Pro Leu Glu Glu Gln Phe Ser Leu
1               5                   10                  15

Ser Ser Tyr Gly Thr Ser Asp Phe Phe Val Ser Ser Ala Tyr Ser Arg
            20                  25                  30

Leu Pro Pro His Thr Gln Pro Val Phe Ser Lys Arg Val Ile Leu Phe
        35                  40                  45

Leu Trp Ser Phe Leu Val Leu Lys Pro Leu Glu Met Val Ala Ala Gly
    50                  55                  60

Met Tyr Tyr Gly Leu Thr Gly Arg Val Val Ala Pro Ala Cys Ile Leu
65                  70                  75                  80

Ala Ala Ile Val Gly Tyr Tyr Val Thr Trp Ala Val Arg Ala Leu Leu
                85                  90                  95

Leu Tyr Val Asn Ile Lys Arg Asp Arg Leu Pro Leu Ser Ala Pro Val
            100                 105                 110

Phe Trp Gly Met Ser Val Phe Leu Gly Gly Thr Ala Leu Cys Ala Leu
        115                 120                 125

Phe Ala Ala Ala His Glu Thr Phe Ser Pro Asp Gly Leu Phe His Phe
    130                 135                 140

Ile Ala Thr Asn Gln Met Leu Pro Pro Thr Asp Pro Leu Arg Thr Arg
145                 150                 155                 160

Ala Leu Gly Ile Ala Cys Ala Ala Gly Ala Ser Met Trp Val Ala Ala
                165                 170                 175

Ala Asp Ser Phe Ala Ala Ser Ala Asn Phe Phe Leu Ala Arg Phe Trp
            180                 185                 190

Thr Arg Ala Ile Leu Asn Ala Pro Val Ala Phe
        195                 200
```

<210> SEQ ID NO 7
<211> LENGTH: 903
<212> TYPE: DNA
<213> ORGANISM: Artificial Sequence
<220> FEATURE:
<223> OTHER INFORMATION: Synthetic sequence derived from HSV-1(F)

<400> SEQUENCE: 7

```
atgctcgccg tccgttccct gcagcacctc tcaaccgtcg tcttgataac ggcgtacggc     60
ctcgtgctcg tgtggtacac cgtcttcggt caccccccca cgggggctg gcgcaaccac    120 gcccatatct gctacgccaa tcttatcgcg ggtagggtcg tgcccttcca ggtcccaccc    180
gacgccatga atcgtcggat catgaacgtc cacgaggcag ttaactgtct ggagaccta     240 tggtacacac gggtgcgtct ggtggtcgta gggtggttcc tgtatctggc gttcgtcgcc    300
```

```
ctccaccaac gccgatgtat gtttggtgtc gtgagtcccg cccacaagat ggtggccccg    360
gccacctacc tcttgaacta cgcaggccgc atcgtatcga gcgtgttcct gcagtacccc    420
tacacgaaaa ttacccgcct gctctgcgag ctgtcggtcc agcggcaaaa cctggttcag    480
ttgtttgaga cggacccggt caccttcttg taccaccgcc ccgccatcgg ggtcatcgta    540
ggctgcgagt tgatgctacg ctttgtggcc gtgggtctca tcgtcggcac cgctttcata    600
tcccgggggg catgtgcaat cacataccc ctgtttctga ccatcaccac ctggtgtttt    660
gtctccacca tcggcctgac agagctgtat tgtattctgc ggcggggccc ggcccccaag    720
aacgcagaca aggccgccgc cccggggcga tccaaggggc tgtcgggcgt ctgcgggcgc    780
tgctgttcca tcatcctctc gggcatcgca gtgcgattgt gttatatcgc cgtggtggcc    840
ggggtggtgc tcgtggcgct tcactacgag caggagatcc agaggcgcct gtttgatgta    900
tga                                                                  903
```

<210> SEQ ID NO 8
<211> LENGTH: 300
<212> TYPE: PRT
<213> ORGANISM: Artificial Sequence
<220> FEATURE:
<223> OTHER INFORMATION: Synthetic sequence derived from HSV-1(F)

<400> SEQUENCE: 8

```
Met Leu Ala Val Arg Ser Leu Gln His Leu Ser Thr Val Val Leu Ile
1               5                   10                  15

Thr Ala Tyr Gly Leu Val Leu Val Trp Tyr Thr Val Phe Gly His Pro
            20                  25                  30

Pro Asn Gly Gly Trp Arg Asn His Ala His Ile Cys Tyr Ala Asn Leu
        35                  40                  45

Ile Ala Gly Arg Val Val Pro Phe Gln Val Pro Asp Ala Met Asn
    50                  55                  60

Arg Arg Ile Met Asn Val His Glu Ala Val Asn Cys Leu Glu Thr Leu
65                  70                  75                  80

Trp Tyr Thr Arg Val Arg Leu Val Val Gly Trp Phe Leu Tyr Leu
                85                  90                  95

Ala Phe Val Ala Leu His Gln Arg Arg Cys Met Phe Gly Val Val Ser
            100                 105                 110

Pro Ala His Lys Met Val Ala Pro Ala Thr Tyr Leu Leu Asn Tyr Ala
        115                 120                 125

Gly Arg Ile Val Ser Ser Val Phe Leu Gln Tyr Pro Tyr Thr Lys Ile
    130                 135                 140

Thr Arg Leu Leu Cys Glu Leu Ser Val Gln Arg Gln Asn Leu Val Gln
145                 150                 155                 160

Leu Phe Glu Thr Asp Pro Val Thr Phe Leu Tyr His Arg Pro Ala Ile
                165                 170                 175

Gly Val Ile Val Gly Cys Glu Leu Met Leu Arg Phe Val Ala Val Gly
            180                 185                 190

Leu Ile Val Gly Thr Ala Phe Ile Ser Arg Gly Ala Cys Ala Ile Thr
        195                 200                 205

Tyr Pro Leu Phe Leu Thr Ile Thr Thr Trp Cys Phe Val Ser Thr Ile
    210                 215                 220

Gly Leu Thr Glu Leu Tyr Cys Ile Leu Arg Arg Gly Pro Ala Pro Lys
225                 230                 235                 240

Asn Ala Asp Lys Ala Ala Ala Pro Gly Arg Ser Lys Gly Leu Ser Gly
                245                 250                 255
```

```
Val Cys Gly Arg Cys Cys Ser Ile Ile Leu Ser Gly Ile Ala Val Arg
            260                 265                 270

Leu Cys Tyr Ile Ala Val Val Ala Gly Val Val Leu Val Ala Leu His
            275                 280                 285

Tyr Glu Gln Glu Ile Gln Arg Arg Leu Phe Asp Val
            290                 295                 300

<210> SEQ ID NO 9
<211> LENGTH: 222
<212> TYPE: PRT
<213> ORGANISM: Herpes Simplex Virus 2

<400> SEQUENCE: 9

Met Thr Met Arg Asp Asp Val Pro Leu Leu Asp Arg Glu Leu Val Asp
1               5                   10                  15

Glu Ala Ala Cys Gly Gly Glu Asp Gly Glu Leu Pro Leu Asp Glu Gln
            20                  25                  30

Phe Ser Leu Ser Ser Tyr Gly Thr Ser Asp Phe Phe Val Ser Ser Ala
        35                  40                  45

Tyr Ser Arg Leu Pro Pro His Thr Gln Pro Val Phe Ser Lys Arg Val
    50                  55                  60

Val Met Phe Ala Trp Ser Phe Leu Val Leu Lys Pro Leu Glu Leu Val
65                  70                  75                  80

Ala Ala Gly Met Tyr Tyr Gly Trp Thr Gly Arg Ala Val Ala Pro Ala
                85                  90                  95

Cys Ile Ile Ala Ala Val Leu Ala Tyr Tyr Val Thr Trp Leu Ala Arg
            100                 105                 110

Ala Leu Leu Leu Tyr Val Asn Ile Lys Arg Asp Arg Leu Pro Leu Ser
        115                 120                 125

Pro Pro Val Phe Trp Gly Leu Cys Val Ile Met Gly Gly Ala Ala Leu
    130                 135                 140

Cys Ala Leu Val Ala Ala Ala His Glu Thr Phe Ser Pro Asp Gly Leu
145                 150                 155                 160

Phe His Trp Ile Thr Ala Ser Gln Leu Leu Pro Arg Thr Asp Pro Leu
                165                 170                 175

Arg Ala Arg Ser Leu Gly Ile Ala Cys Ala Ala Gly Ala Ala Met Trp
            180                 185                 190

Val Ala Ala Ala Asp Cys Phe Ala Ala Phe Thr Asn Phe Phe Leu Ala
        195                 200                 205

Arg Phe Trp Thr Arg Ala Ile Leu Lys Ala Pro Val Ala Phe
    210                 215                 220

<210> SEQ ID NO 10
<211> LENGTH: 338
<212> TYPE: PRT
<213> ORGANISM: Herpes Simplex Virus 2

<400> SEQUENCE: 10

Met Leu Ala Val Arg Ser Leu Gln His Leu Thr Thr Val Ile Phe Ile
1               5                   10                  15

Thr Ala Tyr Gly Leu Val Leu Ala Trp Tyr Ile Val Phe Gly Ala Ser
            20                  25                  30

Pro Leu His Arg Cys Ile Tyr Ala Val Arg Pro Ala Gly Ala His Asn
        35                  40                  45

Asp Thr Ala Leu Val Trp Met Lys Ile Asn Gln Thr Leu Leu Phe Leu
    50                  55                  60
```

```
Gly Pro Pro Thr Ala Pro Gly Gly Ala Trp Thr Pro His Ala Arg
 65                  70                  75                  80

Val Cys Tyr Ala Asn Ile Ile Glu Gly Arg Ala Val Ser Leu Pro Ala
                 85                  90                  95

Ile Pro Gly Ala Met Ser Arg Arg Val Met Asn Val His Glu Ala Val
            100                 105                 110

Asn Cys Leu Glu Ala Leu Trp Asp Thr Gln Met Arg Leu Val Val Val
            115                 120                 125

Gly Trp Phe Leu Tyr Leu Ala Phe Val Ala Leu His Gln Arg Arg Cys
            130                 135                 140

Met Phe Gly Val Val Ser Pro Ala His Ser Met Val Ala Pro Ala Thr
145                 150                 155                 160

Tyr Leu Leu Asn Tyr Ala Gly Arg Ile Val Ser Ser Val Phe Leu Gln
                165                 170                 175

Tyr Pro Tyr Thr Lys Ile Thr Arg Leu Leu Cys Glu Leu Ser Val Gln
            180                 185                 190

Arg Gln Thr Leu Val Gln Leu Phe Glu Ala Asp Pro Val Thr Phe Leu
            195                 200                 205

Tyr His Arg Pro Ala Ile Gly Val Ile Val Gly Cys Glu Leu Leu Leu
210                 215                 220

Arg Phe Val Ala Leu Gly Leu Ile Val Gly Thr Ala Leu Ile Ser Arg
225                 230                 235                 240

Gly Ala Cys Ala Ile Thr His Pro Leu Phe Leu Thr Ile Thr Thr Trp
                245                 250                 255

Cys Phe Val Ser Ile Ile Ala Leu Thr Glu Leu Tyr Phe Ile Leu Arg
            260                 265                 270

Arg Gly Ser Ala Pro Lys Asn Ala Glu Pro Ala Ala Pro Arg Gly Arg
            275                 280                 285

Ser Lys Gly Trp Ser Gly Val Cys Gly Arg Cys Cys Ser Ile Ile Leu
            290                 295                 300

Ser Gly Ile Ala Val Arg Leu Cys Tyr Ile Ala Val Val Ala Gly Val
305                 310                 315                 320

Val Leu Val Ala Leu Arg Tyr Glu Gln Glu Ile Gln Arg Arg Leu Phe
                325                 330                 335

Asp Leu

<210> SEQ ID NO 11
<211> LENGTH: 9
<212> TYPE: PRT
<213> ORGANISM: Herpes Simplex Virus 1

<400> SEQUENCE: 11

Ser Leu Pro Ile Thr Val Tyr Tyr Ala
1               5

<210> SEQ ID NO 12
<211> LENGTH: 9
<212> TYPE: PRT
<213> ORGANISM: Herpes Simplex Virus 2

<400> SEQUENCE: 12

Ser Ile Pro Ile Thr Val Tyr Tyr Ala
1               5

<210> SEQ ID NO 13
<211> LENGTH: 15
```

<212> TYPE: PRT
<213> ORGANISM: Herpes Simplex Virus 1

<400> SEQUENCE: 13

Tyr Thr Ser Thr Leu Leu Pro Pro Glu Leu Ser Glu Thr Pro Asn
1               5                   10                  15

<210> SEQ ID NO 14
<211> LENGTH: 15
<212> TYPE: PRT
<213> ORGANISM: Herpes Simplex Virus 2

<400> SEQUENCE: 14

Tyr Thr Ser Thr Leu Leu Pro Pro Glu Leu Ser Asp Thr Thr Asn
1               5                   10                  15

<210> SEQ ID NO 15
<211> LENGTH: 9
<212> TYPE: PRT
<213> ORGANISM: Herpes Simplex Virus 1

<400> SEQUENCE: 15

Ala Leu Leu Glu Asp Pro Val Gly Thr
1               5

<210> SEQ ID NO 16
<211> LENGTH: 9
<212> TYPE: PRT
<213> ORGANISM: Herpes Simplex Virus 2

<400> SEQUENCE: 16

Ala Leu Leu Glu Asp Pro Ala Gly Thr
1               5

<210> SEQ ID NO 17
<211> LENGTH: 15
<212> TYPE: PRT
<213> ORGANISM: Herpes Simplex Virus 1

<400> SEQUENCE: 17

His Val Asn Asp Met Leu Gly Arg Ile Ala Val Ala Trp Cys Glu
1               5                   10                  15

<210> SEQ ID NO 18
<211> LENGTH: 15
<212> TYPE: PRT
<213> ORGANISM: Herpes Simplex Virus 1

<400> SEQUENCE: 18

Ala Thr Met Tyr Tyr Lys Asp Val Thr Val Ser Gln Val Trp Phe
1               5                   10                  15

<210> SEQ ID NO 19
<211> LENGTH: 8
<212> TYPE: PRT
<213> ORGANISM: Herpes Simplex Virus 1

<400> SEQUENCE: 19

Ser Ser Ile Glu Phe Ala Arg Leu
1               5

<210> SEQ ID NO 20
<211> LENGTH: 22
<212> TYPE: DNA
<213> ORGANISM: Artificial Sequence

```
<220> FEATURE:
<223> OTHER INFORMATION: Primer

<400> SEQUENCE: 20
acgtacctgc ggctcgtgaa ga                                              22

<210> SEQ ID NO 21
<211> LENGTH: 27
<212> TYPE: DNA
<213> ORGANISM: Artificial Sequence
<220> FEATURE:
<223> OTHER INFORMATION: Probe

<400> SEQUENCE: 21
agccaagggc tcctgtaagt acgccct                                         27

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
tcaccccctg ctggtaggcc                                                 20

<210> SEQ ID NO 23
<211> LENGTH: 24
<212> TYPE: DNA
<213> ORGANISM: Artificial Sequence
<220> FEATURE:
<223> OTHER INFORMATION: Primer

<400> SEQUENCE: 23
ccgcgggtac gtacctgcgg ctag                                            24

<210> SEQ ID NO 24
<211> LENGTH: 27
<212> TYPE: DNA
<213> ORGANISM: Artificial Sequence
<220> FEATURE:
<223> OTHER INFORMATION: Probe

<400> SEQUENCE: 24
ggcccgcgcc tcctgcaagt acgctct                                         27

<210> SEQ ID NO 25
<211> LENGTH: 25
<212> TYPE: DNA
<213> ORGANISM: Artificial Sequence
<220> FEATURE:
<223> OTHER INFORMATION: Primer

<400> SEQUENCE: 25
gccctgttgg taggccttcg aggtg                                           25
```

VACCINES AGAINST GENITAL HERPES SIMPLEX INFECTIONS

CROSS REFERENCE TO RELATED APPLICATIONS

This application is the U.S. National Stage of International Application PCT/US2015/029905, filed May 8, 2015, which designates the U.S. and was published by the International Bureau in English on Nov. 12, 2015, and which claims the benefit of U.S. Provisional Application No. 61/990,975, filed May 9, 2014; all of which are whereby incorporated herein in their entirety by reference

FEDERALLY SPONSORED RESEARCH OR DEVELOPMENT

This invention was made with United States Government support under grant number AI 043000 awarded by the National Institutes of Health. The United States Government has certain rights in the invention.

REFERENCE TO A SEQUENCE LISTING SUBMITTED AS A TEXT FILE

The official copy of the sequence listing is submitted electronically via EFS-Web as an ASCII formatted sequence listing with a file named 070114-0006SEQLST.TXT, created on May 7, 2015, and having a size of 21.6 kilobytes, and is filed concurrently with the specification. The sequence listing contained in this ASCII formatted document is part of the specification and is herein incorporated by reference in its entirety.

FIELD OF THE INVENTION

The present invention relates to the field of vaccines for treating or preventing a herpes simplex virus infection.

BACKGROUND OF THE INVENTION

Genital herpes has a very high global prevalence and disease burden. Recent seroprevalence studies for the years 2005-2010 indicate that 1 out of 2 adults in the United States ages 14-49 years old is latently infected with herpes simplex type-1 (HSV-1) (Bradley et al. (2013) *J. Infect. Dis.* 209: 325-333). Most infected individuals experience frequent, but asymptomatic episodes of virus shedding that contribute to high virus transmission rates (Hofstetter et al. (2014) *Curr. Opin. Infect. Dis.* 27:75-83; Tronstein et al. (2011) *JAMA* 305:1441-1449; Mertz (2008) *J. Infect. Dis.* 198: 1098-1100). An increasing number of HSV-1 rather than HSV-2 infections are being observed in clinical cases (Roberts et al. (2003) *Sex. Transm. Dis.* 30:797-800). Importantly, genital HSV infection is considered a risk factor for acquiring human immunodeficiency virus infection (HIV) (Anuradha et al. (2008) *Indian J. Dermatol. Venereol. Leprol.* 74:230-233; Mugo et al. (2011) *Sex. Transm. Dis.* 38:1059-1066; Reynolds et al. (2003) *J. Infect. Dis.* 187: 1513-1521; Renzi et al. (2003) *J. Infect Dis.* 187:19-25; Wald and Link (2002) *J. Infect. Dis.* 185:45-52; Sartori et al. (2011) *Virol. J.* 8:166), and in some geographical areas HSV-2 infection may be a contributing factor to 30-50% of new HIV infections (Brown et al. (2007) *AIDS* 21:1515-1523; Freeman et al. (2006) *AIDS* 20:73-83). A successful vaccination strategy against HSV-2 infection is predicted to have a dramatic global impact on HIV spread, prevention of genital clinical disease and neonatal infections (Freeman et al. (2009) *Vaccine* 27:940-946; Johnston et al. (2014) *Vaccine* 32:1553-1560; Gottlieb et al. (2014) *Vaccine* 32:1527-1535). Prior HSV immunity may confer only partial protection against HSV re-infection and the appearance of clinical disease symptoms (Hofstetter et al. (2014) *Curr. Opin. Infect. Dis.* 27:75-83; Blank and Haines (1973) *J. Invest. Dermatol.* 61:223-225). Adaptive immune responses, particularly tissue specific $CD4^+$ and $CD8^+$ T cells are crucial for controlling HSV infections and clearing the virus after initial infection. These T cell responses are also important in containing the virus in a latent state in ganglionic or dorsal neurons, as well as for controlling the virus after reactivation from latency (Koelle et al. (1998) *J. Clin. Invest.* 101:1500-1508; Milligan et al. (1998) *J. Immunol.* 160:6093-6100; Schiffer and Corey (2013) *Nat. Med.* 19:280-290; Wakim et al. (2008) *Immunol. Cell Biol.* 86:666-675; Zhu et al. (2007) *J. Exp. Med.* 204:595-603; Dudley et al. (2000) *Virology* 270:454-463; St. Leger and Hendricks (2011) *J. Neurovirol.* 17:528-534). Humoral responses have also been implicated in playing an important role in controlling HSV infectivity, spread, and the rate of reactivation from latency (Li et al. (2011) *PNAS* 108:4388-4393; Morrison et al. (2001) *J. Virol* 75:1195-1204; Seppanen et al. (2006) *J. Infect. Dis.* 194: 571-578).

A number of vaccine approaches and candidates have been evaluated in laboratory animals and humans including purified peptides, recombinant glycoprotein subunits, inactivated, live attenuated, replication competent and replication defective whole virus, as well as DNA-based vaccines administered via different routes of immunization (reviewed in: Koelle and Corey (2003) *Clin. Microbiol. Rev.* 16:96-113; Roth et al. (2012) *Microb. Pathog.* 58:45-54; Rupp and Bernstein (2008) *Expert. Opin. Emerg. Drugs* 13:41-52; Dropulic and Cohen (2012) *Expert Rev. Vaccines* 11:1429-1440; and Zhu et al. (2014) *Viruses* 6:371-390). In a double-blind controlled, randomized efficacy field trial of a gD-2 HSV vaccine adjuvanted with A04 (Herpevac Trial) in 8323 women, it was found that the vaccine was 82% protective against HSV-1 genital disease, but offered no significant protection against HSV-2 genital disease (Belshe et al. (2012)*N. Engl. J. Med.* 366:34-43). This protection correlated with induction of neutralizing antibody against gD-2, while cellular immune responses did not appear to be involved in the observed protection (Belshe et al. (2014) *J. Infect. Dis.* 209:828-836; Awasthi and Friedman (2014) *J. Infect. Dis.* 209:813-815). A newer subunit vaccine approach currently in phase I/IIa clinical trials is based on an attempt to generate a balanced T cell and antibody response through the use of T-cell epitopes derived from the ICP4 protein and antibody generated by the gD2 glycoprotein in conjunction with the proprietary adjuvant Matrix-M (Roth et al. (2012) *Microb. Pathog.* 58:45-54).

In principle, live attenuated vaccines have distinct advantages over subunit and inactivated vaccines, primarily because replication of the pathogen allows for the entire repertoire of pathogen-specific antigen expression. Given the 83% nucleotide identity shared by both HSV-1 and HSV-2 genomes (Dolan et al. (1998) *J. Virol* 72:2010-2021), cross protective immunity may be achieved by a single safe and efficacious vaccine expressing a large enough repertoire of cross-protective antigens. Attempts at generating a live attenuated HSV vaccine have focused on the preparation of attenuated viruses that can generate robust immune responses, while minimizing potential virulence in the host. Generally, entire genes that play important roles in the virus lifecycle have been deleted or otherwise modified to attenuate the virus and allow a more robust production of humoral and cellular immune responses. Viral genome modifications include deletions in glycoprotein E (gE) (Brittle et al. (2008) *J. Virol* 82:8431-8441; Awasthi et al. (2012) *J. Virol* 86:4586-4598), multiple deletions in γ34.5, UL55-56, UL43.5, US10-12 (Prichard et al. (2005) *Vaccine* 23:5424-5431), UL5, UL29, UL42, ICP27 genes (van Lint et al. (2007) *Virology* 368:227-231; Dudek et al. (2008) *Virology* 372:165-175; Hoshino et al. (2008) *Vaccine* 26:4034-4040; Da Costa et al. (2001) *Virology* 288:256-263), deletion of ICP0-(Halford et al. (2011) *PLoS One* 6: e17748) and the UL9 gene (Akhrameyeva et al. (2011) *J. Virol* 85:5036-5047; Brans et al. (2009) *J. Invest. Dermatol.* 129:2470-2479; Brans and Yao (2010) *BMC Microbiol.* 10:163; Augustinova et al. (2004) *J. Virol* 78:5756-5765). Other live virus vaccines under study include the HSV-1 virus CJ9-gD engineered to overexpress gD1 and having a dominant negative mutation to prevent virus replication. This vaccine strain has been reported to protect guinea pigs from HSV-2 intravaginal challenge, with marked reduction in vital titer and lesion formation (Brans and Yao (2010) *BMC Microbiol.* 10:163).

Generation of a safe and effective replication competent HSV-1 virus is important to not only vaccinate against acquiring HSV infection and reduce HIV prevalence, but also as a safe vaccine vector that could be utilized for expression of heterologous antigens from other pathogens. HSV has many non-essential genes and can stably carry large fragments of foreign DNA. This genetic flexibility is ideal for the expression of antigens specific to other pathogens (Murphy et al. (2000) *J. Virol* 74:7745-7754; Watanabe et al. (2007) *Virology* 357:186-198). Already recombinant HSV expressing granulocyte monocyte colony stimulating factor (GM-CSF), a potent chemokine functioning in the maturation of macrophages, is being used combined with other chemotherapeutics for the treatment of squamous cell cancer of the head and neck with promising phase I/II results (Harrington et al. (2010) *Clin. Cancer Res.* 16:4005-4015). FDA approval for this particular HSV vaccine therapy for melanoma is expected to pave the way for the use of live-attenuated HSV-based vectors for vaccination against HSV and other pathogens. See also, U.S. Pat. App. Pub. Nos. 2013/0202639 and 2010/0297085.

BRIEF SUMMARY OF THE INVENTION

The present invention provides vaccines for treating or preventing a herpes simplex virus (HSV) infection. The vaccines of the invention comprise recombinant HSVs. A recombinant HSV of the present invention comprises a recombinant HSV genome, particularly a recombinant genome that is derived from the genome of a herpes simplex virus type 1 (HSV-1) or a herpes simplex virus type 2 (HSV-2). In one embodiment of the invention, the vaccines comprise attenuated, recombinant HSVs that are capable of replication in a host cell and incapable of entry into axonal compartments of neurons. The recombinant HSV genomes of the present invention have been engineered to comprise at least one modification in each of the UL53 and UL20 genes. The modifications in the UL53 and UL20 genes include, for example, insertions, substitutions, and deletions of one or more nucleotides that result in changes in the nucleotide sequence of each of these genes.

The present invention further provides methods of immunizing a patient against an HSV infection comprising the step of administering to the patient a therapeutically effective amount vaccine of the present invention.

Additionally provided are recombinant HSV genomes and compositions comprising a recombinant HSV genome of the present invention including, but not limited to, viruses and immunogenic compositions. Methods for producing vaccines, immunogenic compositions, and viruses comprising a recombinant HSV genome of the present invention are also provided.

BRIEF DESCRIPTION OF THE DRAWINGS

FIG. 1 is a schematic of the construction of VC2. FIG. 1A: The top line represents the prototypic arrangement of the HSV-1 genome, with the unique long (UL) and unique short (US) regions flanked by the terminal repeat (TR) and internal repeat (IR) regions. Shown below are the expanded genomic regions which encompass the open reading frames of UL20 and glycoprotein K. In black are the approximate deletions within their respective genes. FIG. 1B: A graphical depiction of the glycoprotein K (gK)-UL20 complex interacting with gB. Areas between the black lines on the graphical depiction represent the approximate location of the deletion in their respective genes.

FIG. 2 depicts the results of in-vitro analysis of the replication and entry characteristics of VC2 vs F BAC. FIG. 2A: Plaque morphology of VC2 vs F BAC on VERO cells 48 hours post infection visualized by IHC and developed with NovaRED substrate. FIG. 2B: Growth curve representative of the replication kinetics of VC2 vs F BAC at both and low (0.1) and high (5) multiplicity of infection (MOI). Samples collected at times 0, 2, 4, 6, 9, 12, 18, 24, and 36 hours post infection titrated on VERO cells. FIG. 2C: Entry assay depicting VC-2 vs F BAC into Chinese hamster ovary (CHO) cells expressing known herpes virus entry receptors PILRa, nectin-1, HVEM, and NEO for a negative control.

FIG. 3 provides graphical representations of pre- and post-challenge morbidity. FIG. 3A: Pre challenge percent change in weight in Mock vs vaccinated animals. Percentages normalized to the initial weight at day 0.  $p \leq 0.01$. Bars represent the 95% confidence interval about the mean. Statistical comparison conducted by SAS using Proc Mixed Type 3 Tests of Fixed Effects. FIG. 3B: Clinical scoring of mice previously receiving mock IM vaccination or $10^7$ PFU IM vaccination of VC2. Two groups (Mock and Vaccinated n=10 each) received a intravaginal challenge of $10^6$ PFU of HSV-2 (G) and 2 groups (Mock and Vaccinated n=10 each) received a intravaginal challenge of $10^6$ PFU of HSV-1 (McKrae). Mice were scored on a scale of 0-6 (0=no disease, 1=ruffled fur and generalized morbidity, 2=mild genital erythema and edema, 3=moderate genital inflammation, 4=genital inflammation with purulent discharge, 5=hind limb paralysis, 6=death).

FIG. 5 provides Kaplan-Meier survival curves. Vaccinated and mock-vaccinated mice in challenge groups were challenged thorough the intra-vaginal route with $10^6$ PFU of HSV-1 McKrae (FIG. 5A) or HSV-2G (FIG. 5B) 21 days post primary vaccination and observed for 14 days. One hundred percent of the vaccinated animals in the HSV-1 and HSV-2 challenged group survived, while 100% of the mock-vaccinated animals died. FIG. 5A: A statistically significant difference was observed between the vaccinated and mock-vaccinated groups (p<0.0001) using the Gehan-Breslow-Wilcoxin test. FIG. 5B: A statistically significant difference was observed between the vaccinated and mock-vaccinated groups (p<0.0001) using the Gehan-Breslow-Wilcoxin test.

FIG. 6 provides graphical representations of vaginal shedding post challenge. FIG. 6A: HSV-1 shedding post challenge in mock vs vaccinated animals. FIG. 6B: HSV-2 shedding post challenge in mock vs vaccinated animals. Significant differences in shed titers noted as * p≤0.05,  p≤0.01, or * p≤0.0001. Bars represent the 95% confidence interval about the mean. Statistical comparison conducted by SAS using The Mixed Procedure Type 3 Tests of Fixed Effects.

FIG. 7 provides graphical representations of in-vitro analysis of humoral immune response. FIG. 7A: Colorimetric ELISA based analysis of HSV-1 reactive polyclonal IgG produced 21 days post vaccination n=20. Statistical comparison conducted by SAS using the T test Procedure. Bars represent the 95% confidence interval about the mean. FIG. 7B: Titration of serum neutralizing fixed PFU of HSV-1 (McKrae) normalized to a no serum control n=5. Significant reduction in PFU observed 1:160, 1:80, 1:40, and 1:20 dilutions of the sera. Statistical comparison conducted by SAS using The Mixed Procedure and Differences in Least Squares Means. Bars represent the 95% confidence interval about the mean.

FIG. 8 provides graphical representations of in-vitro analysis of cellular immune response. FIG. 8A: Proliferation of CD4+ vs CD8+ T cells from mice which received the vaccine and mice which were mock injected and stimulated with pooled HSV-1 or HSV-2 peptides. (FIGS. 8B-8F) CBA analysis of secreted cytokine concentration in cell culture supernatant from T cell proliferation assay. Statistical comparison conducted by SAS using The Mixed Procedure and Differences in Least Squares Means. Bars represent the 95% confidence interval about the mean. Significant differences noted as * p≤0.05,  p≤0.01, or * p≤0.0001.

SEQUENCE LISTING

Figure 3C:
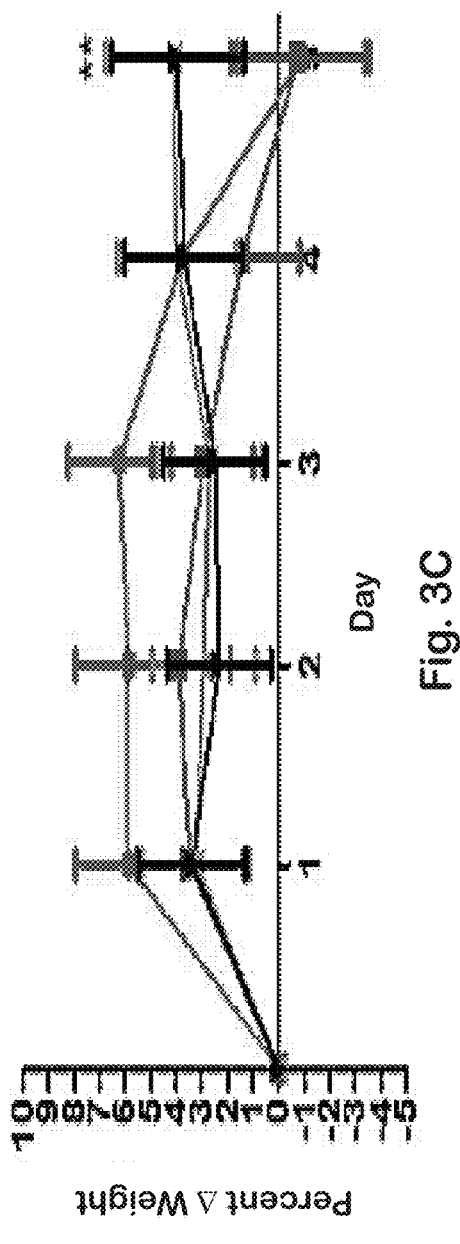
FIG. 3C: Percent change in weights post challenge in Mock vs vaccinated animals challenged with either HSV-1 (McKrae) or HSV-2 (G). Percentages normalized to the initial weight at day 0.  $p \leq 0.01$. Bars represent the 95% confidence interval about the mean. Statistical comparison conducted by SAS using Proc Mixed Type 3 Tests of Fixed Effects.

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. The amino acid sequences follow the standard convention of beginning at the amino terminus of the sequence and proceeding forward (i.e., from left to right in each line) to the carboxy terminus.

SEQ ID NO: 1 sets forth the nucleotide sequence of the UL20 gene of human herpes simplex virus 1, strain F ("HSV-1(F)"). The entire genome of HSV-1 strain F is publicly available as GenBank Accession No. GU734771.1. The GenBank database can be accessed on the World Wide Web at ncbi.nlm.nih.gov/genbank.

SEQ ID NO: 2 sets forth the amino acid sequence of the UL20 protein that is encoded by the UL20 gene of HSV-1 (F).

SEQ ID NO: 3 sets forth the nucleotide sequence of the UL53 gene of HSV-1(F).

SEQ ID NO: 4 sets forth the amino acid sequence of glycoprotein K (gK), which is encoded by UL53 gene of HSV-1(F).

SEQ ID NO: 5 sets forth the nucleotide sequence of the modified UL20 gene of VC2.

SEQ ID NO: 6 sets forth the amino acid sequence of the modified UL20 protein that is encoded by the modified UL20 gene of VC2.

SEQ ID NO: 7 sets forth the nucleotide sequence of the modified UL53 gene of VC2.

SEQ ID NO: 8 sets forth the amino acid sequence of the modified gK that is encoded by modified UL53 gene of VC2.

SEQ ID NO: 9 sets forth the amino acid sequence of the UL20 protein that is encoded by the UL20 gene of HSV-2. The complete genome of HSV-2 including, but not limited to, the nucleotide sequence of the UL20 gene is publicly available as GenBank Accession No. NC_001798.1

SEQ ID NO: 10 sets forth the amino acid sequence of glycoprotein K (gK), which is encoded by UL53 gene of HSV-2. The complete genome of HSV-2 including, but not limited to, the nucleotide sequence of the UL53 gene is publicly available as GenBank Accession No. NC_001798.1.

SEQ ID NOS: 11-19 set forth the amino acid sequences of the peptides shown in Table 2.

SEQ ID NOS: 20-25 set forth the nucleotide sequences of the PCR primers described below in the Example.

DETAILED DESCRIPTION OF THE INVENTION

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The present invention provides vaccines for treating or preventing an HSV infection in an animal that is capable of being infected with an HSV, particularly a mammal, more particularly a human. In one embodiment, the present invention provides vaccines that are useful for treating or preventing a herpes simplex virus type 1 (HSV-1) infection, a herpes simplex virus type 2 (HSV-2) infection, or an infection with both HSV-1 and HSV-2. HSV-1 and HSV-2 establish life-long infections and cause significant orofacial and genital infections in humans. HSV-1 is the leading cause of infectious blindness in the western world. Currently, there are no available vaccines to protect against herpes simplex infections. The vaccines of the present invention comprises a recombinant HSV, particularly a recombinant HSV-1, that has been engineered to be incapable of entry into axonal compartments of neurons in a host while be capable of efficient replication in a host cell. The vaccines of the present invention find use in treating and/or preventing orofacial and genital HSV infections in humans.

The vaccines of the present invention comprise a recombinant HSV that was been genetically engineered to contain certain modifications in its genome. The recombinant HSV comprises a recombinant HSV genome that comprises at least one modification in each of the UL53 and UL20 genes. A recombinant HSV genome of the present invention is a non-naturally occurring HSV genome that is produced by methods that are disclosed elsewhere herein. A recombinant HSV of the present invention is an HSV comprising a recombinant HSV genome of the invention.

In the genome of HSV-1, the UL53 gene encodes glycoprotein K (gK), and the UL20 gene encodes the UL20 protein. Both gK and the UL20 protein are membrane proteins and are known to form a complex that interacts with glycoprotein B (gB), another HSV-1 encoded membrane protein. It is known that the amino terminal regions of both gK and the UL20 protein interact with gB and that these interactions modulate virus-induced cell fusion mediated by the gK/UL20 protein complex. For the present invention, the modifications in the UL53 and UL20 genes are those that cause changes in the amino acid sequences of the gK and the UL20 protein, respectively. The modifications in the UL53 and UL20 genes include, for example, insertions, substitutions, and/or deletions of one or more nucleotides, which cause insertions, substitutions, and/or deletions of one or more amino acids in the proteins encoded thereby. In preferred embodiments of the invention, the vaccines comprise live, attenuated, recombinant HSVs.

While the present invention does not depend on a particular biological mechanism, it is believed that the modifications in the gK and the UL20 protein disrupt or otherwise negatively affect the interaction of the wild-type gK/UL20 protein complex with wild-type gB. Preferred modifications are modifications in the portions of gK and/or the UL20 protein that disrupt or otherwise negatively affect the interaction of the wild-type gK/UL20 protein complex with wild-type gB, including, for example, the amino terminal regions of both gK and the UL20 protein. More preferred modifications are deletions of amino acids in the amino terminal regions of gK and/or the UL20 protein that disrupt or otherwise negatively affect the interaction of the wild-type gK/UL20 protein complex with wild-type gB. In one embodiment of the invention involving modifications to the genome of HSV-1 strain F, ("HSV-1(F)"), the modification in the UL53 gene (SEQ ID NO: 3) is a deletion of nucleotides, which corresponds to a deletion of nucleotides 112160 to 112274 in the genome of HSV-1(F), and which results in the deletion of amino acids 31 to 68 (SEQ ID NO: 4) in the amino terminal region of gK and the modification the UL20 gene (SEQ ID NO: 1) is a deletion of nucleotides 10 to 66, which corresponds to a deletion of nucleotides 41339 to 41395 in the genome of HSV-1(F), respectively, and which results in the deletion of amino acids 4 to 22 (SEQ ID NO: 2) in the amino terminal region of the UL20 protein. In another embodiment of the invention involving modifications to the genome of HSV-1 strain F, ("HSV-1(F)"), the modification in the UL53 gene (SEQ ID NO: 3) is a deletion of nucleotides, which corresponds to a deletion of nucleotides 112160 to 112274 in the genome of HSV-1(F), and which results in the deletion of amino acids 31 to 68 (SEQ ID NO 4) in the amino terminal region of gK and the modification the UL20 gene (SEQ ID NO: 1) is a deletion of nucleotides 10 to 81, which corresponds to a deletion of nucleotides 41324 to 41395, in the genome of HSV-1(F), and which results in the deletion of amino acids 4 to 27 (SEQ ID NO: 2) in the amino terminal region of the UL20 protein.

Other preferred modifications to the UL20 protein include, for example, the deletions of amino acids 4-23, 4-24, 4-25, and 4-26 from a native or wild-type UL20 protein (SEQ ID NO:2).

A preferred recombinant HSV genome of the present invention is the VC2 genome. The VC2 genome, which is derived from the genome of HSV-1(F), comprises the deletion of nucleotides 112160 to 112274 from the genome of HSV-1(F), which results in the deletion of amino acids 31 to 68 in the amino terminal region of gK and the deletion of nucleotides 41339 to 41395 from the genome of HSV-1, which results in the deletion of amino acids 4-22 in the amino terminal region of the UL20 protein. A virus comprising the VC2 genome is referred to herein as "VC2" or a "VC2 virus". The nucleotide and amino acid sequences corresponding to UL20 and UL53 genes of VC2 are set forth in SEQ ID NOS: 1-4.

The gK and the UL20 proteins of HSV-2 are known to have a high degree of identity with, and identical overall predicted 3-dimensional structures to, the corresponding gK and the UL20 proteins of HSV-1. Moreover, it is known that the gKΔ31-68 deletion spans a β-sheet domain in the amino terminus of gK that is conserved between HSV-1 and HSV-2. Therefore, it is expected that similar deletions in the gK and UL20 proteins of HSV-2 will function the same as the deletions in the gK and UL20 proteins of HSV-1. Thus, the present invention encompasses the same modifications in the gK and UL20 proteins of HSV-2 as described above for the gK and UL20 proteins of HSV-1.

In an embodiment of the invention involving modifications to the genome of HSV-2, the modification in the UL53 gene is a deletion which results in the deletion of amino acids 31 to 68 (SEQ ID NO: 10) in the amino terminal region of gK and the modification the UL20 gene is a deletion which results in the deletion of amino acids 4 to 22 (SEQ ID NO: 9) in the amino terminal region of the UL20 protein. In another embodiment of the invention involving modifications to the genome of HSV-2, the modification in the UL53 gene is a deletion which results in the deletion of amino acids 31 to 68 (SEQ ID NO 10) in the amino terminal region of gK and the modification the UL20 gene is a deletion which results in the deletion of amino acids 4 to 27 (SEQ ID NO: 9) in the amino terminal region of the UL20 protein. Other preferred modifications to the UL20 protein of HSV-2 include, for example, the deletions of amino acids 4-23, 4-24, 4-25, and 4-26 from a native or wild-type gK protein (SEQ ID NO: 9)

The present invention involves making modifications to an HSV genome, so as to produce a recombinant HSV genome. Preferably, the HSV genome that is modified is an HSV-1 or HSV-2 genome. More preferably, the HSV genome that is modified is an HSV-1 genome. Most preferably, the HSV genome that is modified is an HSV-1(F) genome. The modifications can be made by any one of more of the methods known in the art for modifying a nucleic acid molecule including, for example, restriction endonuclease digestion, polymerase chain reaction (PCR) amplification, site-directed mutagenesis, ligation, chemical DNA synthesis, and the like. A recombinant HSV of the present invention that is produced by modifying a particular HSV genome can also be referred to being derived from that particular HSV genome. Typically, the HSV genome that is modified by methods of the present invention is a naturally occurring or wild-type HSV genome. However, in certain embodiments, the HSV genome that is modified by methods of the present invention has been previously modified through human intervention involving the use of, for example, recombinant DNA methods or mutagenesis methods involving mutagens such as, for example, chemical mutagens and radiation.

The present invention further provides the recombinant HSV genomes and recombinant HSV viruses described above as well as immunogenic compositions comprising at least one recombinant HSV genome of the present invention. In some embodiments, the immunogenic compositions comprise a recombinant HSV genome that is contained within a recombinant HSV virus. In other embodiments, the immunogenic compositions comprise a recombinant HSV genome that is not contained within a recombinant HSV virus The vaccines and other immunogenic compositions of the present invention can comprise a live recombinant HSV and/or an inactivated recombinant HSV. Preferably, the vaccines of the present invention comprise a live, attenuated recombinant HSV.

The vaccines and immunogenic compositions can further comprise one or more pharmaceutically acceptable components including, but not limited to, a carrier, an excipient, a stabilizing agent, a preservative, an immunostimulant, and an adjuvant. Each of the pharmaceutically acceptable components is present in the vaccines and immunogenic compositions in a pharmaceutically acceptable amount. Such a pharmaceutically acceptable amount is an amount that is sufficient to produce the desired result (e.g. the amount of stabilizer sufficient to stabilize the vaccine after making and until administration) but is considered safe for administration to an animal, particularly a human.

The present invention further provides methods of immunizing a patient against an HSV infection comprising the step of administering to the patient a therapeutically effective amount vaccine of the present invention. Preferably, the patient is an animal. More preferably, the patient is a human.

A "therapeutically effective amount" as used herein refers to that amount which provides a therapeutic effect for a given condition and administration regimen. In particular aspects of the invention, a "therapeutically effective amount" refers to an amount of a vaccine or other immunogenic composition of the invention that, when administered to an animal, brings about a positive therapeutic response with respect to the prevention or treatment of the animal for an HSV infection. A positive therapeutic response with respect to preventing an HSV infection includes, for example, the production of HSV antibodies by the animal in a quantity sufficient to protect against development of disease caused by the HSV. Similarly, a positive therapeutic response in regard to treating an HSV infection includes curing or ameliorating the symptoms of the disease. The phrase "therapeutically effective amount" is used herein to mean an amount sufficient to cause an improvement in a clinically significant condition in an animal, particularly a human.

In some embodiments of the methods of the invention, the therapeutically effective amount of a vaccine of the invention is administered to the patient in a single dose. In other embodiments, the vaccine is administered to the patient in multiple doses. It is recognized that the therapeutically effective amount of a vaccine of the invention can vary depending on the dosing regimen and can even vary from one administration to the next in multiple dosing regimens.

The present invention additionally provides methods for producing a recombinant HSV. The methods comprising transfecting a host cell with the recombinant HSV genome of the present invention and incubating the transfected host cell under conditions favorable for the formation of a recombinant HSV virus comprising the recombinant HSV genome, whereby a recombinant HSV is produced. Preferably, the host cell is an animal cell and can be either a host cell contained in an animal or an in-vitro-cultured animal cell including, for example, an in-vitro cultured human cell. The conditions under which the transfected host cell is incubated will depend on a number of factors including, but not limited to, the particular host cell, the amount of the recombinant HSV genome that is transfected into the host cell, and the particular HSV that is produced from the recombinant HSV genome. It is recognized that those of skill in the art can determine empirically the optimal conditions for producing a recombinant HSV of the present invention in a transfected host cell by methods described elsewhere herein or otherwise known in the art. The methods can further comprise the optional step of purifying the recombinant HSV virus by separating the recombinant HSV from the cellular components of the host cell using standard methods that are known in the art. In a preferred embodiment, the recombinant HSV comprises a recombinant HSV genome comprising the deletion of nucleotides 41339 to 41395 and 112160 to 112274 from the genome of HSV-1(F) (GenBank Accession No. GU734771.1). Such a recombinant HSV genome encodes both a modified gK in which amino acids 31 to 68 in the amino terminal region of gK from HSV-1(F) have been deleted and a modified UL20 protein in which amino acids 4-22 in the amino terminal region of the UL20 protein from HSV-1(F) have been deleted. The amino acid sequences of the modified UL20 protein and the modified gK are set forth in SEQ ID NOS: 6 and 8, respectively. Examples of nucleotide sequences encoding the modified UL20 protein and the modified gK are set forth in SEQ ID NOS: 5 and 7, respectively. The VC2 genome of the invention comprises the nucleotide sequences of the modified UL20 and UL58 genes set forth in SEQ ID NOS: 5 and 7, respectively.

Further provided are methods for producing a vaccine or immunogenic composition. The methods involve producing the recombinant HSV essentially as described above. In particular, the methods for producing a vaccine or immunogenic composition comprise transfecting a host cell with the recombinant HSV genome of the invention, incubating the transfected host cell under conditions favorable for the formation of a recombinant HSV virus comprising the recombinant HSV genome, purifying the recombinant HSV virus comprising the recombinant HSV genome, and optionally, combining the purified recombinant HSV virus with at least one pharmaceutically acceptable component.

Because it is known that the HSV genome can accommodate additional DNA and still form viruses when transfected into a host cell, the compositions and methods of the present invention also find use in treating and preventing diseases that are caused by other viral and bacterial pathogens. In certain embodiments of the invention one or more genes encoding a protein antigen from another viral and/or bacterial pathogen is added to a recombinant HSV of the present invention. Transfection of such a recombinant HSV genome into a host cell and incubation of the transfected host cell under conditions favorable for the formation of a recombinant HSV virus results in the production of the antigen(s) in the host cell, whereby an immune response is elicited in the host cell. Thus, a recombinant HSV genome of the present invention can be utilized as a vector for expression of other viral and bacterial pathogens. In one embodiment of the invention, the recombinant HSV genome is the VC2 genome described above and further comprises an additional gene, preferably an additional gene encoding an antigen, particularly a foreign antigen. Foreign antigens expressed in a host cell from the VC2 genome are expected to provide a strong adjuvant effect causing the generation of protective adaptive immune responses against mucosally transmitted pathogens such as HIV and *Chlamydia trachomatis*. Unless stated otherwise or apparent from the context of use, a foreign antigen for the present invention is an antigen that is not encoded by a genome of the host cell.

The vaccines and other immunogenic compositions of the present invention can comprise one or more pharmaceutically acceptable components including, but not limited to, a carrier, an excipient, a stabilizing agent, a preservative, an immunostimulant, and an adjuvant. In general, a pharmaceutically acceptable component does not itself induce the production of an immune response in the animal receiving the component and can be administered without undue toxicity in composition of the present invention. As used herein, the term "pharmaceutically acceptable" means being approved by a regulatory agency of the Federal or a state government or listed in the U.S. Pharmacopia, European Pharmacopia or other generally recognized pharmacopia for use in vertebrates, and more particularly in humans. These compositions can be useful as a vaccine and/or antigenic compositions for inducing a protective immune response in a vertebrate.

Carriers include but are not limited to saline, buffered saline, dextrose, water, glycerol, sterile isotonic aqueous buffer, and combinations thereof. A thorough discussion of pharmaceutically acceptable carriers, diluents, and other excipients is presented in Remington's Pharmaceutical Sciences (Mack Pub. Co. N.J. current edition), herein incorporated in its entirety by reference. The formulation should suit the mode of administration. In a preferred embodiment, the formulation is suitable for administration to humans, preferably is sterile, non-particulate and/or non-pyrogenic.

Examples of stabilizing agents, immunostimulants, and adjuvants include alum, incomplete Freud's adjuvant, MR-59 (Chiron), muramyl tripeptide phosphatidylethanolamide, and mono-phosphoryl Lipid A. Preservatives include, for example, thimerosal, benzyl alcohol, and parabens. Such stabilizing agents, adjuvants, immune stimulants, and preservatives are well known in the art and can be used singly or in combination.

Pharmaceutically acceptable components can include, for example, minor amounts of wetting or emulsifying agents, or pH buffering agents. The composition can be a solid form, such as a lyophilized powder suitable for reconstitution, a liquid solution, suspension, emulsion, tablet, pill, capsule, sustained release formulation, or powder. Oral formulation can include standard carriers such as pharmaceutical grades of mannitol, lactose, starch, magnesium stearate, sodium saccharine, cellulose, magnesium carbonate, and the like.

Certain methods of the invention involve administering a therapeutically effective amount of a vaccine or other immunogenic composition to a patient. The methods of the present invention do not depend of a particularly method of administering the vaccine or other immunogenic composition to the patient. For example, the vaccine or other immunogenic composition can be administered orally, intradermally, intranasally, intramusclarly, intraperitoneally, intravenously, or subcutaneously using routine methods known in the art or disclosed elsewhere herein.

The recombinant HSV genomes of the present invention comprise nucleotide sequences which are modified by methods disclosed herein or otherwise known in the art so as to produce a recombinant HSV genome. In one embodiment of the invention, the recombinant HSV genome comprises: (a) the modified UL20 and UL53 genes set forth in SEQ ID NOS: 5 and 7, respectively, (b) a nucleotide sequence encoding the modified UL20 protein and the modified gK having the amino acid sequences set forth in SEQ ID NOS: 6 and 8, respectively, or (c) a variant nucleotide sequence comprising at least one modification in each of the UL53 and UL20 genes, wherein a virus comprising the recombinant HSV genome capable of replication in a host cell and incapable of entry into axonal compartments of neurons. Such variants include, for example, recombinant HSV genomes that are derived from the genome of HSV-1(F), another strain of HSV-1, or a strain of HSV-2. Preferably, the UL20 and UL53 genes of such variants have at least about 80%, 85%, 90%, 91%, 92%, 93%, 94%, 95%, 96%, 97%, 98%, 99% or more sequence identity to the full-length nucleotide sequences set forth in SEQ ID NOS: 5 and 7, respectively, and/or the UL20 and UL53 genes of such variants encode UL20 and gK proteins having at least about 80%, 85%, 90%, 91%, 92%, 93%, 94%, 95%, 96%, 97%, 98%, 99% or more sequence identity to the full-length amino acid sequences set forth in SEQ ID NOS: 6 and 8, respectively.

The present invention encompasses isolated or substantially purified polynucleotide (also referred to herein as "nucleic acid molecule", "nucleic acid" and the like) or protein (also referred to herein as "polypeptide") compositions. An "isolated" or "purified" polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A protein that is substantially free of cellular material includes preparations of protein having less than about 30%, 20%, 10%, 5%, or 1% (by dry weight) of contaminating protein. When the protein of the invention or biologically active portion thereof is recombinantly produced, optimally culture medium represents less than about 30%, 20%, 10%, 5%, or 1% (by dry weight) of chemical precursors or non-protein-of-interest chemicals.

"Variants" is intended to mean substantially similar sequences. For polynucleotides, a variant comprises a polynucleotide having deletions (i.e., truncations) at the 5' and/or 3' end; deletion and/or addition of one or more nucleotides at one or more internal sites in the native polynucleotide; and/or substitution of one or more nucleotides at one or more sites in the native polynucleotide. As used herein, a "native" polynucleotide or polypeptide comprises a naturally occurring nucleotide sequence or amino acid sequence, respectively. Generally, variants of a particular recombinant HSV genome of the invention will have at least about 80%, 85%, 90%, 91%, 92%, 93%, 94%, 95%, 96%, 97%, 98%, 99% or more sequence identity to the recombinant HSV genome as determined by sequence alignment "Variant" protein is intended to mean a protein derived from the native protein by deletion (so-called truncation) of one or more amino acids at the N-terminal and/or C-terminal end of the native protein; deletion and/or addition of one or more amino acids at one or more internal sites in the native protein; or substitution of one or more amino acids at one or more sites in the native protein. Such variants may result from, for example, genetic polymorphism or from human manipulation. Biologically active variants of a protein will have at least about 80%, 85%, 90%, 91%, 92%, 93%, 94%, 95%, 96%, 97%, 98%, 99% or more sequence identity to the amino acid sequence for the native protein as determined by sequence alignment programs and parameters described elsewhere herein. A biologically active variant of a protein of the invention may differ from that protein by as few as 1-15 amino acid residues, as few as 1-10, such as 6-10, as few as 5, as few as 4, 3, 2, or even 1 amino acid residue.

The proteins of the invention may be altered in various ways including amino acid substitutions, deletions, and insertions. Methods for such manipulations are generally known in the art. Methods for mutagenesis and polynucleotide alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

The deletions, insertions, and substitutions of the protein sequences encompassed herein are not expected to produce radical changes in the characteristics of the protein except for those changes that are disclosed herein. However, when it is difficult to predict the exact effect of the substitution, deletion, or insertion in advance of doing so, one skilled in the art will appreciate that the effect will be evaluated by routine screening assays. That is, the activity can be evaluated by assays that are disclosed hereinbelow.

Variant polynucleotides and proteins also encompass sequences and proteins derived from a mutagenic and recombinogenic procedure such as DNA shuffling. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

PCR amplication methods can be used in making the recombinant HSV genomes of the present invention. Methods for designing PCR primers and PCR cloning are generally known in the art and are disclosed in Sambrook et al. (1989)*Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

It is recognized that the recombinant HSV genomes of the present invention encompass other nucleic acid molecules comprising a nucleotide sequence that is sufficiently identical to a nucleotide sequence disclosed herein. The term "sufficiently identical" is used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common structural domain and/or common functional activity. For example, amino acid or nucleotide sequences that contain a common structural domain having at least about 80% identity, preferably or 85% identity, more preferably 90% or 95% identity, most preferably 96%, 97%, 98% or 99% identity, are defined herein as sufficiently identical.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. A preferred, nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the NBLAST and XBLAST programs of Altschul et al. (1990) *J. Mol. Biol.* 215:403. BLAST nucleotide searches can be performed with the NBLAST program, score=100, wordlength=12, to obtain nucleotide sequences homologous to the polynucleotide molecules of the invention. BLAST protein searches can be performed with the XBLAST program, score=50, wordlength=3, to obtain amino acid sequences homologous to protein molecules of the invention. To obtain gapped alignments for comparison purposes, Gapped BLAST can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., XBLAST and NBLAST) can be used. LAST, Gapped BLAST, and PSI-Blast, XBLAST and NBLAST are available on the World Wide Web at ncbi.nlm.nih.gov. Another preferred, non-limiting example of a mathematical algorithm utilized for the comparison of sequences is the algorithm of Myers and Miller (1988) *CABIOS* 4:11-17. Such an algorithm is incorporated into the ALIGN program (version 2.0), which is part of the GCG sequence alignment software package. When utilizing the ALIGN program for comparing amino acid sequences, a PAM120 weight residue table, a gap length penalty of 12, and a gap penalty of 4 can be used. Alignment may also be performed manually by inspection.

Unless otherwise stated, sequence identity/similarity values provided herein refer to the value obtained using the full-length sequences of the invention using BLAST with the default parameters; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by BLAST using default parameters.

As used herein, the term "operably linked" is intended to mean a functional linkage between two or more elements. For example, an operable linkage between a polynucleotide or gene of interest and a regulatory sequence (i.e., a promoter) is functional link that allows for expression of the polynucleotide of interest. Operably linked elements may be contiguous or non-contiguous. When used to refer to the joining of two protein coding regions, by operably linked is intended that the coding regions are in the same reading frame.

As used herein unless stated otherwise or apparent from the context of usage, a host cell is an animal cell, preferably a mammalian cell, more preferably a human cell. Similarly, a host or host organism is an animal, preferably a mammal, more preferably a human.

Non-limiting examples of the compositions and methods disclosed herein are as follows:

1. A vaccine for treating or preventing a herpes simplex virus (HSV) infection, the vaccine comprising a recombinant HSV, wherein the recombinant HSV comprises a recombinant HSV genome comprising at least one modification in each of the UL53 and UL20 genes and wherein the recombinant HSV is capable of replication in a host cell and incapable of entry into axonal compartments of neurons.

2. The vaccine of 1, wherein the recombinant HSV genome is derived from the genome of HSV-1 or HSV-2.

3. The vaccine of 2, wherein HSV-1 is HSV-1 strain F.

4. The vaccine of any one of 1-3, wherein the at least one modification is selected from the group consisting of an insertion, a substitution, and a deletion.

5. The vaccine of any one of 2-4, wherein the modified UL53 gene comprises a deletion.

6. The vaccine of any one of 2-5, wherein the modified UL20 gene comprises a deletion.

7. The vaccine of 5 or 6, wherein the deletion in the modified UL53 corresponds to the portion of the UL53 gene encoding the amino terminal region of glycoprotein K (gK).

8. The vaccine of any one of 5-7, wherein the deletion in the modified UL53 gene corresponds to the region of the UL53 gene that encodes amino acids 31-68 of wild-type gK.

9. The vaccine of any one of 6-8, wherein the deletion in the modified UL20 gene corresponds to the portion of the UL20 gene encoding the amino terminal region of the UL20 protein.

10. The vaccine of 6-9, wherein the deletion in the modified UL20 gene corresponds to the region of the UL20 gene that encodes amino acids 4-22 of wild-type UL20 protein.

11. The vaccine of any one of 1-10, wherein the genome comprises a member selected from the group consisting of:
 (a) the nucleotide sequence set forth in SEQ ID NO: 5;
 (b) a nucleotide sequence comprising at least 90% identity to the nucleotide sequence set forth in SEQ ID NO: 5;
 (c) a nucleotide sequence encoding the amino acid sequence set forth in SEQ ID NO: 6;
 (d) a nucleotide sequence encoding an amino acid sequence comprising at least 90% identity to the amino acid sequence set forth in SEQ ID NO: 6;
 (e) the nucleotide sequence set forth in SEQ ID NO: 7;
 (f) a nucleotide sequence comprising at least 90% identity to the nucleotide sequence set forth in SEQ ID NO: 7;
 (g) a nucleotide sequence encoding the amino acid sequence set forth in SEQ ID NO: 8;
 (h) a nucleotide sequence encoding an amino acid sequence comprising at least 90% identity to the amino acid sequence set forth in SEQ ID NO: 8; and
 (i) the nucleotide sequence of (a), (b), (c), or (d) and the nucleotide sequence of (e), (f), (g), or (h).

12. The vaccine of any one of 1-11, wherein the recombinant HSV is a live virus.

13. The vaccine of any one of 1-12, wherein the HSV infection comprises a genital HSV infection.

14. The vaccine of any one of 1-13, wherein the HSV infection comprises or further comprises an orofacial HSV infection.

15. The vaccine of any one of 1-14, further comprising a pharmaceutically acceptable component selected from the group consisting of a carrier, an excipient, a stabilizing agent, a preservative, an immunostimulant, and an adjuvant.

16. A method of immunizing a patient against an HSV infection comprising the step of administering to the patient a therapeutically effective amount vaccine of any one of 1-15.

17. The method of 16, wherein the patient is a human.

18. An recombinant herpes simplex virus (HSV) genome comprising at least one modification in each of the UL53 and UL20 genes and wherein a virus comprising the genome is capable of replication in a host cell and incapable of entry into axonal compartments of neurons.

19. The recombinant HSV genome of 18, wherein the recombinant HSV genome is derived from the genome of HSV-1 or HSV-2.

20. The recombinant HSV genome of 19, wherein HSV-1 is HSV-1 strain F.

21. The recombinant HSV genome of any one of 18-20, wherein the at least one modification is selected from the group consisting of an insertion, a substitution, and a deletion.

22. The recombinant HSV genome of any one of 19-21, wherein the modified UL53 gene comprises a deletion.

23. The recombinant HSV genome of any one of 19-22, wherein the modified UL20 gene comprises a deletion.

24. The recombinant HSV genome of 22 or 23, wherein the deletion in the modified UL53 gene corresponds to the portion of the UL53 gene encoding the amino terminal region of glycoprotein K (gK).

25. The recombinant HSV genome of any one of 22-24, wherein the deletion in the modified UL53 gene corresponds to the region of the UL53 gene that encodes amino acids 31-68 of wild-type gK.

26. The recombinant HSV genome of any one of 23-25, wherein the deletion in the modified UL20 gene corresponds to the portion of the UL20 gene encoding the amino terminal region of the UL20 protein.

27. The recombinant HSV genome of 23-26, wherein the deletion in the modified UL20 gene corresponds to the region of the UL20 gene that encodes amino acids 4-22 of wild-type UL20 protein.

28. The recombinant HSV genome of any one of 18-27, wherein the genome comprises a member selected from the group consisting of:
   (a) the nucleotide sequence set forth in SEQ ID NO: 5;
   (b) a nucleotide sequence comprising at least 90% identity to the nucleotide sequence set forth in SEQ ID NO: 5;
   (c) a nucleotide sequence encoding the amino acid sequence set forth in SEQ ID NO: 6;
   (d) a nucleotide sequence encoding an amino acid sequence comprising at least 90% identity to the amino acid sequence set forth in SEQ ID NO: 6;
   (e) the nucleotide sequence set forth in SEQ ID NO: 7;
   (f) a nucleotide sequence comprising at least 90% identity to the nucleotide sequence set forth in SEQ ID NO: 7;
   (g) a nucleotide sequence encoding the amino acid sequence set forth in SEQ ID NO: 8;
   (h) a nucleotide sequence encoding an amino acid sequence comprising at least 90% identity to the amino acid sequence set forth in SEQ ID NO: 8; and
   (i) the nucleotide sequence of (a), (b), (c), or (d) and the nucleotide sequence of (e), (f), (g), or (h).

29. The recombinant HSV genome of any one of 18-28, further comprising an additional gene.

30. The recombinant HSV genome of 29, wherein the additional gene encodes an antigen.

31. The recombinant HSV genome of 30, wherein the antigen is capable of eliciting an immune response is a host cell against a pathogenic virus or a pathogenic bacterium.

32. The recombinant HSV genome of 31, wherein the pathogenic virus is not HSV.

33. An immunogenic composition comprising the recombinant HSV genome of any one of 18-32.

34. The immunogenic composition of 33, wherein the recombinant HSV genome is contained in a live virus.

35. The immunogenic composition of 33, wherein the recombinant HSV genome is contained in an inactivated virus.

36. The immunogenic composition of any one of 33-35, further comprising at least one pharmaceutically acceptable component selected from the group consisting of a carrier, an excipient, a stabilizing agent, a preservative, an immunostimulant, and an adjuvant.

37. A virus comprising the recombinant HSV genome of any one of 18-32.

38. The virus of 37, wherein the virus is an isolated virus.

39. A method for producing a vaccine or immunogenic composition, the method comprising:
   (a) transfecting a host cell with the recombinant HSV genome of any of 18-32;
   (b) incubating the transfected host cell under conditions favorable for the formation of a recombinant HSV virus comprising the recombinant HSV genome;
   (c) purifying the recombinant HSV virus comprising the recombinant HSV genome; and optionally
   (d) combining the purified recombinant HSV virus with at least one pharmaceutically acceptable component.

40. The method of 39, wherein the virus is HSV-1 or HSV-2.

41. A method for producing a recombinant HSV, the method comprising:
   (a) transfecting a host cell with the recombinant HSV genome of any of 18-32; and
   (b) incubating the transfected host cell under conditions favorable for the formation of a recombinant HSV virus comprising the recombinant HSV genome, whereby a recombinant HSV is produced.

42. The method of 41, further comprising purifying the recombinant HSV virus produced in (b).

43. The method of 41 or 42, wherein the virus is HSV-1 or HSV-2.

The following examples are offered by way of illustration and not by way of limitation.

EXAMPLES

Example 1: Development of an Attenuated Herpes Simplex Virus Vaccine

Previously, it was shown that a gK-null virus was unable to infect ganglionic neurons and establish latency after ocular infection of mice (David et al. (2008) *Curr. Eye Res.* 33:455-467; David et al. (2012) *MBio* 3:e00144-00112). It was further shown that intramuscular vaccination of mice with the attenuated gK-null virus conferred significant cellular immune responses and protection against intravaginal challenge of mice with either virulent HSV-1 (McKrae) or HSV-2(G) viruses (Iyer et al. (2013) *Virol. J.* 10:317). To further improve on this vaccination approach, the VC2 mutant virus of the present invention was constructed. The VC2 mutation virus has specific deletions within the genes coding for glycoprotein K (gK) and UL20. The VC2 virus contains the gKΔ31-68 mutation that prevents the virus from infecting ganglionic neurons after ocular infection in mice (Saied et al. K G. (2014) *Curr. Eye Res.* 39:596-603). In contrast to the gK-null virus that requires replication in the complementing cell line VK302 that expresses gK, the VC2 virus can replicate efficiently in infected Vero cells achieving titers similar to that of the wild-type HSV-1(F) parental virus in cell culture (Saied et al. KG. (2014) *Curr. Eye Res.* 39:596-603). Intramuscular injection of mice with 107 VC2 plaque forming units did not cause any significant clinical disease in mice. A single intramuscular vaccination with the VC2 virus was very well tolerated at a high infectious dose ($10^7$ PFU), produced a robust humoral and cell-mediated immune response and conferred 100% sterile immunity against lethal intravaginal challenge with either HSV-1 (McKrae) or HSV-2 (G) viruses. The VC2 virus vaccine elicits strong humoral and cellular immune responses capable of conferring sterile immunity to mice infected via the vaginal route.

Construction and Characterization of the VC2 Vaccine Virus

The VC2 recombinant virus was constructed utilizing the two-step double-Red recombination protocol (Tischer et al. (2006) *Biotechniques* 40:191-197) implemented on the cloned HSV-1(F) genome in a bacterial artificial chromosome (BAC) plasmid (Tanaka et al. (2003) *J. Virol* 77:1382-1391) as described previously (Chouljenko et al. (2009) *J. Virol* 83:12301-12313; Lee et al. (2009) *J. Virol* 83:6115-6124), and detailed in the Materials and Methods section below. The VC2 virus contains the gKΔ31-68 deletion (38 aa; gK aa 31-68) in the amino terminus of gK that prevents the virus from entering into ganglionic neurons after infection via the ocular route (Saied et al. KG. (2014) *Curr. Eye Res.* 39:596-603), as well as a deletion of the amino-terminal 19 amino acids of the UL20 virus (FIG. 1A). Next generation whole genome sequencing was performed to validate that only intended mutations were induced into the HSV-1 (F) BAG. A total sequence output of Q20 quality that is derived from the predicted per-base quality scores and corresponds to an error rate of 1% generated 2666 and 4436 coverage for the two biological replica samples sequenced. A total of 37 nt changes and 13 of that caused aa differences were detected in comparison to the Gene bank submission GU 734771 of human herpes simplex virus type 1 (strain F, complete genome), as reported previously for other HSV-1 (F) BAG mutant viruses (Kim et al. (2013) *J. Virol.* 87: 8029-8037). Overall, there were no nucleotide changes between the parental HSV-1(F) BAG and the derived VG2 mutant virus with the exception of the engineered deletions within the UL20 and gK genes.

It has been previously shown that the amino termini of both gK and UL20 interact with gB and that these interactions modulate virus-induced cell fusion mediated by the gK/UL20 protein complex (Chouljenko et al. (2009) *J. Virol* 83:12301-12313; Chouljenko et al. (2010) *J. Virol* 84:8596-8606; Foster et al. (2008) *J. Virol* 82:6310-6323) (FIG. 1B). The UL20Δ4-22 mutation does not affect virus replication, although it produces a syncytial phenotype (not shown). However, the simultaneous presence of the gKΔ31-68 and UL20Δ4-22 deletions produce an non-syncytial plaque phenotype, which were 30-40% smaller in size than the parental virus (FIG. 2A). The VC2 virus replicated as efficiently as the parental wild-type HSV-1(F) BAC virus at a multiplicity of infection (MOI) of 5. At low MOI (0.1), VC2 replicated with slower kinetics, but achieved similar peak virus titers by 36 hpi (FIG. 2B). The VC2 and HSV-1(F) BAC viruses exhibited similar entry efficiencies into Chinese hamster ovary (CHO) cells expressing the HSV-1 receptors Nectin-1, and HVEM (FIG. 2C). Both HSV-1(F) and VC2 failed to enter into paired immunoglobulin receptor-α (PILRα), expressing CHO cells, as reported previously for HSV-1(F) in comparison to HSV-1 (McKrae) (Chowdhury et al. (2013) *J. Virol* 87:3305-3313).

Figure 3D:
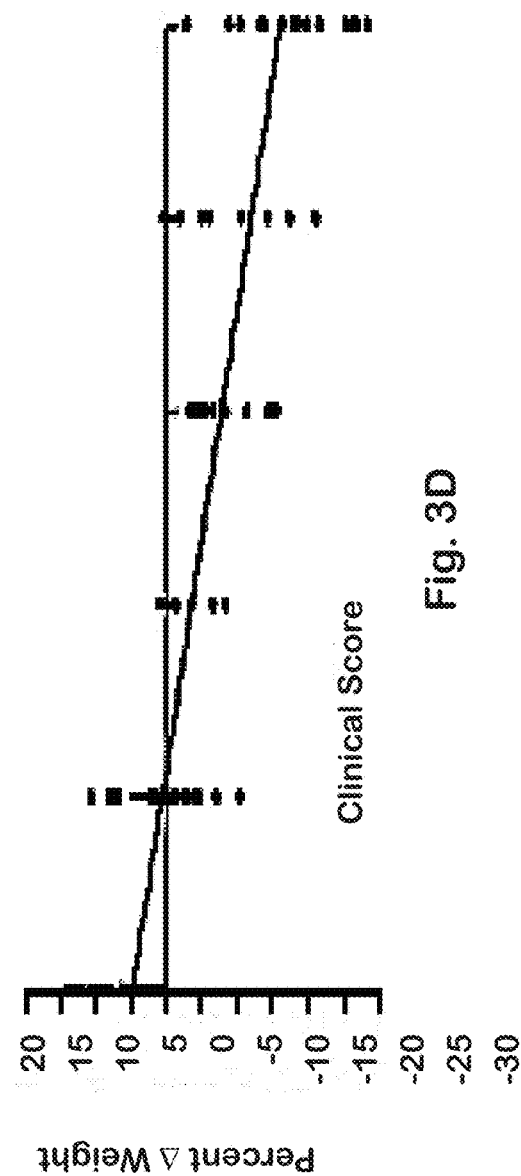
FIG. 3D: Correlation between percent change in weight VS. Clinical score of unvaccinated mice Gaussian Approximation $p<0.0001$ Spearman $r=-0.84108$.
Figure 4B:
FIG. 4 provides photographic illustrations of pathogenesis post challenge. Disease pathology among mock (FIGS. 4A, 4B) and vaccinated (FIGS. 4C, 4D) animals challenged with either HSV-1 (McKrae) or HSV-2 (G) 5 days post challenge. HSV-1 (McKrae) and HSV-2(G) infected mice exhibited similar disease progression and pathology in the mock groups (top two panels). Vaccinated mice (bottom two panels) did not exhibit any clinical disease over the observation period post challenge. Mild disease symptoms included ruffled fur, hunching posture, inflammation and redness of vagina (top right). More serious manifestations included purulent vaginal discharge (top left).
Figure 4D:
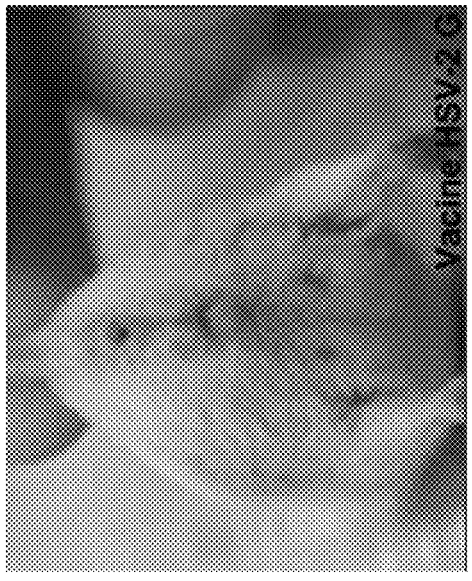
Figure 4A:
Figure 4C:
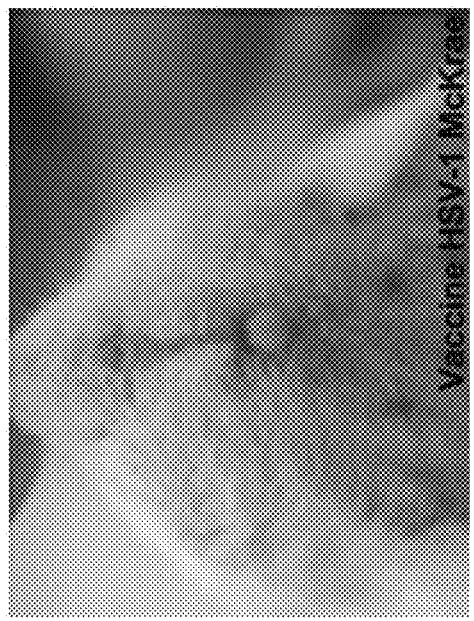

Vaccination and Intravaginal Challenge of VC2 Vaccinated Mice with HSV-1 (McKrae) and HSV-2(G) Viruses Initial safety experiments indicated that the VC2 virus did not produce significant clinical disease symptoms after intranasal or intramuscular injection of nearly $10^7$ PFU per mouse, and there was no viral DNA was detected by PCR in either dorsal or trigeminal ganglia from these mice (not shown). The vaccine strategy involved intramuscular injection of $10^7$ PFU of the VC2 virus in each mouse followed by treatment of mice at day 15 post vaccination via intramuscular injection of Depo Provera, as described previously (Iyer et al. (2013) *Virol. J.* 10:317), and intravaginal challenge with $10^6$ PFU of either HSV-1 (McKrae) or HSV-2(G) viral strains at day 21 post vaccination. VC2 vaccinated mice were monitored for clinical disease symptoms and the body weights were also monitored daily. No significant clinical disease symptoms were noted throughout the 15 day observation period. Also, no significant differences in body weights of vaccinated versus mock-vaccinated animals were observed except on day 14 post vaccination (p<0.05) (FIG. 3A). Following vaginal challenge with either HSV-1 (McKrae) or HSV-2(G), infected mice were observed daily for disease manifestations. For fifteen days following challenge, clinical scores and weight measurement were recorded for all live mice. Mock-vaccinated animals showed pronounced, time-dependent increase in clinical disease symptoms and a significant concomitant decrease in weight by day 5 post challenge (FIG. 3: B, C). Analysis of clinical scores with the corresponding changes in weights of unvaccinated mice revealed a strong correlation between increasing clinical scores and decreasing body weights (FIG. 3D). This correlation analysis revealed that the observed difference in vaccinated versus mock-vaccinated animals on day 10 post vaccination was not indicative of significant overall morbidity. Disease symptoms in the mildest cases consisted primarily of hair loss, hunched posture and fur ruffling (not shown). More advanced disease symptoms included significant vaginal and peri-anal erythema and edema and purulent discharge (FIG. 4). As noted previously (Iyer et al. (2013) *Virol. J.* 10:317), HSV-1 (McKrae) caused significant clinical disease approaching that observed in HSV-2(G) infections (FIG. 4).

Vaccinated mice were completely protected against lethal challenge. Mice in the mock-vaccinated group started dying on day 6 for the HSV-1 challenged group, and day 7 in the HSV-2 challenged group. In both groups of mice, challenged with either HSV-1 or HSV-2, protection against lethal challenge was significantly higher in vaccinated than mock-vaccinated animals (p<0.0001) (FIG. 5). Vaginal shedding was assessed for 4 days following challenge. Significant reductions in virus shedding were observed on all days post challenge in the HSV-1 (days 1, 2: p=0.0002; day 3: p=0.008; day 4: p=0.0244): and HSV-2 group of mice (day 1: p=0.0014; days, 3-4: p<0.0001). In both cases, vaccinated animals did not shed any virus after day 4 post challenge. Overall, lower viral titers were recovered from the vaginas of the HSV-2 than the HSV-1 challenged mice (FIG. 6: A, B).

To determine whether HSV-1 (McKrae), or HSV-2(G) were able to infect ganglionic or dorsal root neurons and establish latent infection, challenged mice were immunocompromised by injection of cyclophosphamide followed by injection of dexamethasone at 100 days post challenge. No infectious virus was recovered from vaginal swabs of vaccinated mice treated with cyclophosphamide and dexamethasone which is known to chemically induce reactivation of virus from latency (Cook et al. (1991) *Invest. Ophthalmol. Vis. Sci.* 32:1558-1561). Similarly, there was no viral DNA detected for either HSV-1 (McKrae) or HSV-2(G) in the extracted neuronal tissues by virus type-specific quantitative PCR (qPCR) for the vaccinated mice; however, tissues from mock-vaccinated animals revealed the presence of either HSV-1 (McKrae) or HSV-2(G) viral DNA in the respective animal groups (Table 1).

TABLE 1 qPCR[1] of Dorsal Root Ganglia from Vaccinated Animals

| HSV-1 Challenge | HSV-1 gD | HSV-2 gD | HSV-2 Challenge | HSV-1 gD | HSV-2 gD |
|---|---|---|---|---|---|
| Positive Control | −1 | — | Positive Control | — | −2 |
| 161 | — | — | 171 | — | — |
| 162 | — | — | 172 | — | — |
| 163 | — | — | 173 | — | — |
| 164 | — | — | 174 | — | — |
| 165 | — | — | 175 | — | — |
| 166 | — | — | 176 | — | — |
| 167 | — | — | 177 | — | — |
| 168 | — | — | 178 | — | — |
| 169 | — | — | 179 | — | — |
| 170 | — | — | 180 | — | — |

[1]qPCR results from sacral dorsal root ganglia excised from vaccinated mice challenged with either HSV-1 (McKrae) or HSV-2 (G). Positive controls were sacral dorsal root ganglia excised from unvaccinated mice challenged with either HSV-1 (McKrae) or HSV-2 (G). Samples below the limit of detection are designated as ND. The qPCR assays specific for either HSV-1 and HSV-2 viral DNA detected as low as 3 viral DNA copies/J.L (see Materials and Methods).

VC2-Induced Humoral and Cellular Immune Responses

Figure 7C:
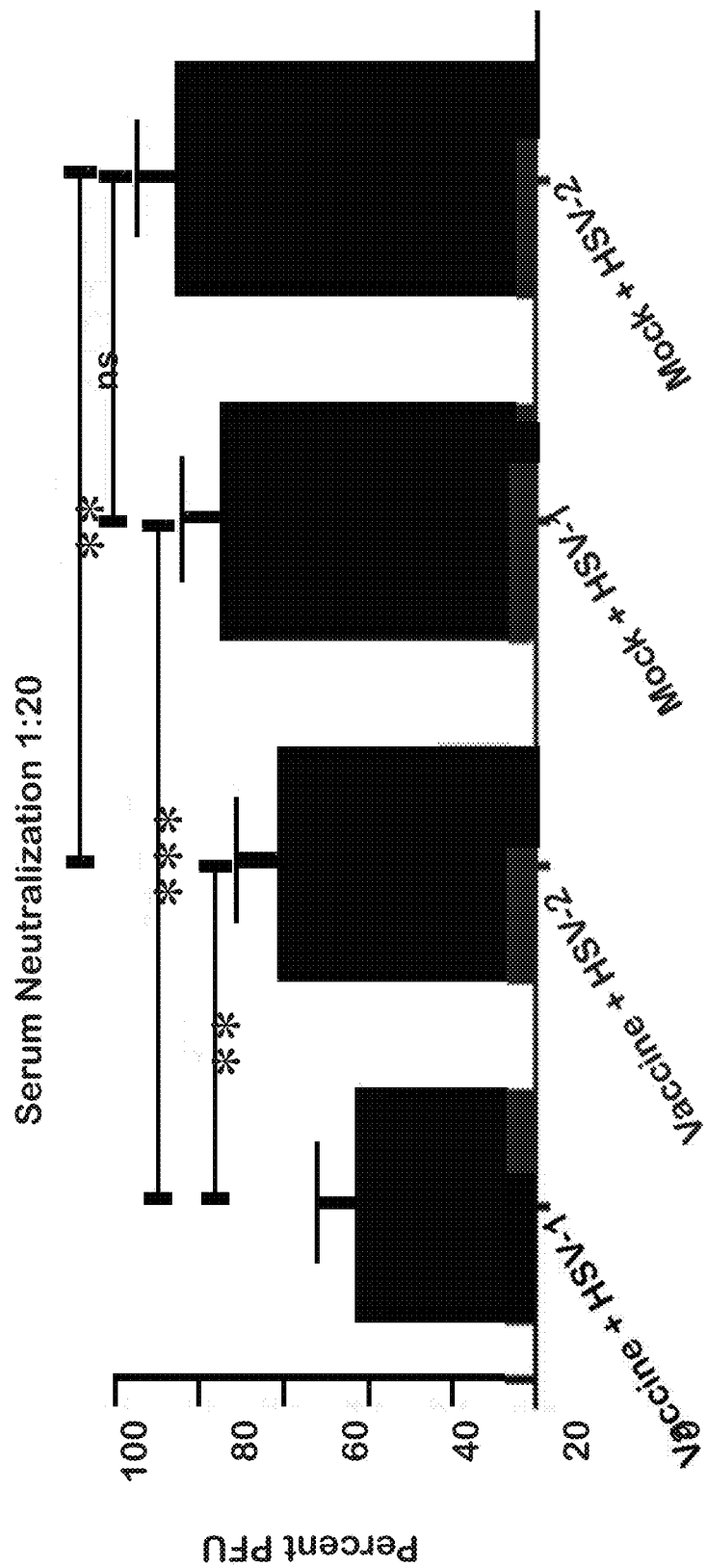
FIG. 7C: Cross reactive neutralization of HSV-1 (McKrae) and HSV-2 (G) at a 1:20 dilution of sera from vaccinated and mock inoculated mice. Percent neutralization normalized to no serum controls. Statistical comparison conducted by SAS using The Mixed Procedure and Differences in Least Squares Means. Bars represent the 95% confidence interval about the mean. Significant differences noted as * p≤0.05,  p≤0.01, or * p≤0.0001.

To assess the relative levels of HSV-1 specific antibodies raised by the VC2 vaccination a commercially available ELISA was utilized to measure the relative quantity of HSV-specific IgG. In this ELISA, plates were coated with HSV-1-infected cell extracts and HSV-1 bound antibodies were quantified by colorimetry (see Materials and Methods). All VC2 vaccinated mice produced HSV-1-specific antibodies, while none of the mock-vaccinated animals produced detectable anti-HSV antibodies (FIG. 7A). The VC-2-induced antibodies were tested for ability to neutralize HSV-1 (McKrae) virus. Antisera from five vaccinated and mock-vaccinated mice were individually tested at serial dilutions for ability to neutralize the virus, as described in Materials and Methods. Substantial neutralization of HSV-1 (McKrae) was noted at 1:160, 1:80, 1:40 and 1:20 dilutions of each mouse serum (FIG. 7B). To further investigate the neutralization activities of these sera, the 1:20 dilution was chosen to test for ability to neutralize both HSV-1 (McKrae) and HSV-2(G). Significant differences were observed between the neutralization of HSV-1 (McKrae) and HSV-2(G) by sera of HSV-1 (VC2)-vaccinated animals in comparison to the mock-vaccinated mice, as well as between HSV-1 (McKrae) and HSV-2(G) vaccinated animals. However, no significant differences were observed between the mock-vaccinated groups (FIG. 7C).

Figure 8C:
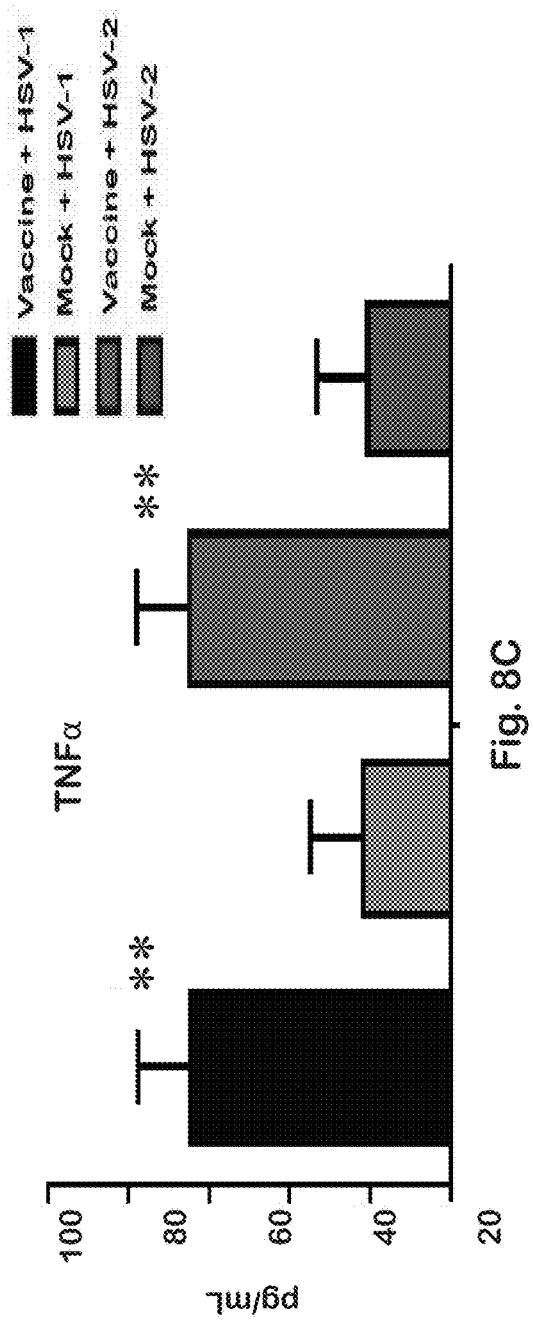
Figure 8D:
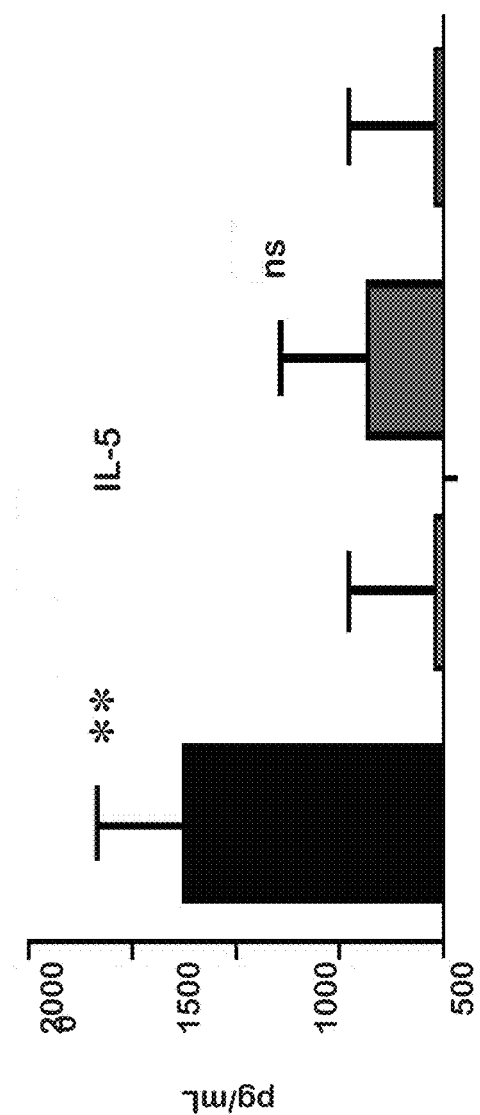

To test for the generation of VC2-specific cellular immune responses, a CFSE-membrane labeling assay was utilized to detect cellular proliferation of $CD4^+$ and $CD8^+$ T cells in the presence of a pool of specific peptides representing known or predicted $CD4^+$ and $CD8^+$ T epitopes (Table 2). Spleenocytes from vaccinated mice produced both CD8+ and CD4+ T cell proliferation, while lymphocytes from mock-vaccinated mice did not respond to the pooled peptide stimuli (FIG. 8A). Additional analysis was performed by determining the relative levels of Th1/Th2 cytokines in response to the peptide pool. Significant induction of IFNγ, TNFα, IL-4 and IL-5 were noted, while IL-2 was not significantly induced in the vaccinated versus mock-vaccinated mice (FIGS. 8B-8F).

TABLE 2

Peptides Used in Pools for Spleenocyte Stimulation Assays

| Virus | Glycoprotein | Locus | Amino Acids | Reference |
|---|---|---|---|---|
| HSV-1 | gD | 70-78 | SLPITVYYA (SEQ ID NO: 11) | J. Immunol. 2010; 184:2561-71 |
| HSV-2 | gD | 77-85 | SIPITVYYA (SEQ ID NO: 12) | NA |
| HSV-1 | gD | 270-287 | YTSTLLPPELSETPN (SEQ ID NO: 13) | NA |
| HSV-2 | gD | 270-287 | YTSTLLPPELSDTTN (SEQ ID NO: 14) | Cell Immunol. 2006; 239:113-20 |
| HSV-1 | gD | 278-286 | ALLEDPVGT (SEQ ID NO: 15) | J. Immunol. 2010; 184:2561-71 |
| HSV-2 | gD | 250-258 | ALLEDPAGT (SEQ ID NO: 16) | NA |
| HSV-1 | gB | 566-580 | HVNDMLGRIAVAWCE (SEQ ID NO: 17) | Vaccine 2011; 29:7058-66 |
| HSV-1/HSV-2 | gB | 161-176 | ATMYYKDVTVSQVWF (SEQ ID NO: 18) | J. Immunol. 2010; 184:2561-71 |
| HSV-1/HSV-2 | gB | 499-506 | SSIEFARL (SEQ ID NO: 19) | J. Immunol. 2011; 186:3927-3933 |

DISCUSSION

Because it was known that gK is necessary for infection of ganglionic neurons after ocular infection, the use of a gK-null virus as a potential vaccine for HSV-1 and HSV-2 genital infection was investigated. This initial work demonstrated that gK-null vaccination produced effective strong cellular immune responses and provided significant protection in mice (Iyer et al. (2013) *Virol. J.* 10:317). However, replication of the gK-null virus requires the use of a complementing cell line, negatively impacting the possibility that this virus could be produced for human use. In contrast, the VC2 engineered virus can efficiently replicate in standard cell cultures, while retaining the in vivo avirulent characteristics of the gK-null virus. The VC2 virus was highly immunogenic and conferred sterile immunity to vaccinated mice against lethal intravaginal challenge with highly virulent HSV-1 and HSV-2 strains.

Construction of the VC2 Virus

It was reported previously that gK forms a functional protein complex with the UL20 membrane protein that is required for their intracellular transport, cell-surface expression and ability to modulate gB-mediate membrane fusion (Foster et al. (2008) *J. Virol* 82:6310-6323; Foster et al. (2004) *J. Virol* 78:13262-13277). Modulation of gB fusogenic properties is mediated via direct protein-protein interactions between the gK and gB amino termini, as well as between the gB carboxyl-terminus and the UL20 amino terminus (Chouljenko et al. (2009) *J. Virol* 83:12301-12313; Chouljenko et al. (2010) *J. Virol* 84:8596-8606). The VC2 virus was constructed based on the hypothesis that disruption of gK/UL20 interaction with gB will lead to viral attenuation. This hypothesis was supported by the fact that deletion of 38 aa from the amino terminus of gK prevented the virus from infecting ganglionic neurons after ocular infection of mice. Serial deletions of amino acids 4-22, 4-27, 4-47 and 4-48 from the amino terminus of the UL20 protein have revealed that amino acids 4-27 are dispensable for virus replication in cell culture with the 4-22 deletion producing similar virus titers to that of the HSV-1(F) parental virus. Therefore, the 4-22 UL20 deletion was engineered into the VC2 virus to provide an additional safety feature because rescue of the VC2 virus by a wild-type genome in vivo would require a double recombination-rescue event to occur. Moreover, disruption of the UL20 amino terminus would provide additional dysregulation of gB functions, as evidenced by the fact that the UL20Δ4-22 mutant virus caused virus-induced cell fusion in cell culture (not shown). However, incorporation of the gKΔ31-68 mutation eliminated the UL20Δ4-22-induced cell fusion providing additional support for our long-standing hypothesis that UL20 and gK cooperate to regulate gB's fusogenic properties primarily through interactions of the amino-termini of gK and gB (Chouljenko et al. (2009) *J. Virol* 83:12301-12313; Chouljenko et al. (2010) *J. Virol* 84:8596-8606). As expected the VC2 virus replicated efficiently in Vero cells in comparison to its parental virus HSV-1(F), while it produced on average smaller viral plaques as has been shown previously for the gKΔ31-68 mutation in both the HSV-1(F) and HSV-1 (McKrae) genetic backgrounds (Saied et al. KG. (2014) *Curr. Eye Res.* 39:596-603; Chouljenko et al. (2009) *J. Virol* 83:12301-12313). Also, the VC2 virus efficiently utilized the nectin-1 and HVEM receptors for virus entry except the PILRαreceptor, as shown previously for the HSV-1(F) virus (Chowdhury et al. (2013) *J. Virol* 87:3305-3313).

Vaccination Experiments

It was previously shown that HSV-1(F) BAC does not cause substantial disease symptoms after ocular infection of mice, in contrast to the highly virulent HSV-1 (McKrae) strain, although both viruses are readily transmitted to ganglionic neurons and establish latency (Saied et al. KG. (2014) *Curr. Eye Res.* 39:596-603; Kim et al. (2014) *Curr. Eye Res.* 39:1169-77). Consistent with these previously reported results, safety experiments performed by intranasal infection with $10^6$ PFU of either HSV-1(F) BAC or VC2 viruses revealed no apparent clinical symptoms and absence of detectable viral genomes in trigeminal ganglia. Similarly, infectious doses of up to $10^7$ PFU of either HSV-1(F) BAC or VC2 delivered intramuscularly did not produce any significant clinical disease symptoms and there was no viral DNA detected in either trigeminal or dorsal root ganglia of infected mice.

Glycoprotein K has been associated with increased virulence and immunopathogenesis. Specifically, ocular infection of mice previously vaccinated with gK exacerbated corneal immunopathogenesis, while an HSV-1 virus expressing two copies of the gK gene was significantly more virulent than the wild-type virus (Allen et al. (2014) *Invest. Ophthalmol. Vis. Sci.* 55-2442-2451; Allen et al. (2010) *Virology* 399:11-22; Ghiasi H et al. (2000) *Virus Res.* 68:137-144; Mott et al. (2009) *Invest. Ophthalmol. Vis. Sci.* 50:2903-2912; Mott et al. (2007) *J. Virol* 81:12962-12972). Recently, it has been reported that the gKΔ31-68 mutation attenuates the highly virulent ocular HSV-1 (McKrae) strain and prevent infection of trigeminal ganglionic neurons after ocular infection (Saied et al. KG. (2014) *Curr. Eye Res.* 39:596-603). The VC2 vaccine strain contains the gKΔ31-68 mutation, which is expected to attenuate the virus and prevent infection of ganglionic neurons. Therefore, it is reasonable to assume that VC2 is substantially safer than HSV-1(F) BAC, since it contains double gene deletions in gK and UL20 associated with defects in neuronal entry.

In general, live-attenuated viral vaccines mimic natural infections and induce more robust humoral and cellular immune responses against a broad spectrum of viral proteins. In contrast, subunit vaccines can only carry a limited number of immunogenic epitopes and do not directly induce innate immune responses, as is the case with live virus vaccines. Intramuscular immunization with the VC2 virus produced neutralizing antibody against both HSV-1 (McKrae) and HSV-2(G) virus. HSV-1 and HSV-2 share a relatively high degree of protein sequence homology and are known to induce type-common antibodies (cross reactive between HSV-1 and HSV-2) that recognize major antigenic viral determinants, the majority of which constitute sequential and conformational domains of viral glycoproteins (Kousoulas et al. (1988) *Virology* 166:423-431; Pereira et al. (1980) *Infect. Immun.* 29:724-732). Moreover, pre-existing HSV-1 exposure is known to reduce the severity and duration of HSV-2 infection (Koelle and Corey (2003) *Clin. Microbiol. Rev.* 16:96-113) suggesting the elicitation of type-common immune responses.

Assessment of T cell responses was facilitated by the use of pools of selected and well-characterized peptides representing gB and gD-specific CD4+ and CD8+ T cell epitopes, as reported previously (Iyer et al. (2013) *Virol. J.* 10:317), including few more viral peptides (supplemental FIG. 1B). Proliferation of T-cells cultured with pooled peptides is a direct measure of memory T cells capable of recognizing the epitopes present in the peptide pool only. As such, they may underestimate the overall T-cell response against the HSV proteome that is expressed by the VC2 vaccine. As reported previously, the most prominent T cell response observed in gK-null vaccinated mice was from gB-specific CD8+ T cells (specifically peptide 161-176). Interestingly in human patients, this particular T-cell epitope has been identified as immunodominant, recalling the strongest HLA-DR-dependent CD4+ T-cell proliferation and IFN-γ production in contrast to other epitopes (Chentoufi et al. (2008) *J. Virol* 82:11792-11802). The gB (161-176) and gB (499-506) peptide sequences are identical between HSV-1 and HSV-2, therefore, it was hypothesized that immune responses directed toward these two epitopes may contribute to the observed cross-protection against both HSV-1 and HSV-2 infections. In addition, most other peptides utilized for the proliferation assays exhibited a high level of amino acid conservation and homology in the HSV-1 and HSV-2 proteomes suggesting that they may also be involved in the induction of cross-protective immunity.

Intramuscular vaccination with the VC2 virus followed by intra vaginal lethal challenge with either HSV-1 (McKrae) or HSV-2 (G) protected 100% of the vaccinated mice, while all mock-vaccinated mice died. Importantly, infectious virus could not be recovered after immunosuppression of vaccinated and challenged mice and the ganglia of these mice did not contain detectable viral DNA. Collectively these results, with the observed rapid inhibition of virus replication in infected vaginal tissues in vaccinated versus mock-vaccinated mice, suggests that protection against the challenging viruses was conferred largely by limiting virus replication in infected vaginal tissues.

Adaptive immune responses are essential for providing protection against HSV-1 and HSV-2 infections (Dropulic and Cohen (2012) Expert Rev. Vaccines 11:1429-1440; Coleman and Shukla (2013) Hum. Vaccin. Immunother. 9:729-735; Dervillez et al. (2012) Future Virol. 7:371-378). Recently, it was shown that HSV-2-specific CD8+ T cells generated after chemo-attractant therapy given vaginally in mice mediate long-lived protection against HSV-2 challenge (Shin and Iwasaki (2012) Nature 491:463-467). Our observations of the inhibition of viral replication in vaginal tissues within the first 3-4 days post infection suggests that the induction of neutralizing antibodies and the rapid local recruitment of cytotoxic T-cells are sufficient to protect against HSV infection. This theory is supported by the presence of neutralizing IgG antibodies and the development of potent memory T cell pools in the vaccinated mice. Additional studies are needed to assess the level of tissue-specific, intra-vaginal immunity to HSV-1 and HSV-2 infections after a single dose of VC2.

Ideally, a live-attenuated vaccine could be used for both prophylactic and therapeutic purposes. Elicitation of robust tissue-specific T-cell memory responses would confer substantial advantage in limiting replication of reactivated virus, as well as inhibiting secondary infections. It is also possible, that CD8+ T cells may be sufficient to prevent viral reactivation from latently infected neurons. The VC2 virus could be effectively utilized as a vector for expression of other viral and bacterial pathogens. VC2 expressed foreign antigens may take advantage of the innate immune responses elicited by the VC2 virus that lead to a strong adaptive immune response enabling the induction of protective adaptive immune responses against additional mucosally transmitted pathogens such as HIV and Chlamydia trachomatis.

Ideally, a live-attenuated vaccine could be used for both prophylactic and therapeutic purposes. Elicitation of robust tissue-specific T-cell memory responses would confer substantial advantage in limiting replication of reactivated virus, as well as inhibiting secondary infections. It is also likely, that CD8+ T cells may prevent viral reactivation from latently infected neurons. The VC2 virus could be effectively utilized as a vector for expression of other viral and bacterial pathogens. VC2 expressed foreign antigens may provide a strong adjuvant effect causing the generation of protective adaptive immune responses against mucosally transmitted pathogens such as HIV and Chlamydia trachomatis.

In summary, the results disclosed herein demonstrate that an attenuated HSV-1 vaccine has been developed with at least two important properties. First, the vaccine is avirulent because it cannot enter into neurons due to two small deletions in the amino termini of glycoprotein K (gK) and the membrane protein UL20. Second, the vaccine virus when inoculated intramuscularly into mice protected them 100% against lethal intravaginal challenge with either virulent herpes simplex virus type-1 (McKrae) and virulent herpes simplex type-2 (HSV-2G). There were no symptoms of any kind associated with herpetic disease in the challenged mice. Importantly, the vaccinated mice developed "sterile" immunity, since there was not viral HSV-1 (McKrae) or HSV-2G viral DNA detected in the dorsal ganglia of challenged mice. Protection was associated with high neutralizing antibodies against both viruses and induction of robust cytotoxic T cell responses. It is expected that the vaccine will produce similar results in humans.

There is no available vaccine against herpes simplex virus. However, there are at least few vaccines that are being pursued by others, most notably a live-attenuated virus produced by Sanofi-Pasteur. However, the vaccine of the present invention is far superior to the Pasteur-Sanofi virus, since it does not infect neutrons and establish latency and procedures sterile immunity that has never been demonstrated before for any other herpes simplex vaccine.

Materials and Methods

Viruses

VC2 recombinant virus construction was performed using double red recombination system in E. coli SW 105 cells as described previously (Tischer et al. (2006) Biotechniques 40:191-197). Briefly, specific oligonucleotides designed to delete (aa 31-68) within the ORF encoding the HSV-1 gene UL53 (gK) were used first to generate the respective BAC cloned into E. coli. After transfection of the Vero cells the recombinant HSV-1 virus gKΔ31-68 was recovered. Fresh Vero cells were infected with this virus and circular viral DNA was isolated 6 hours post infection (hpi) using the method previously described (Hirt (1967) J. Mol. Biol. 26:365-369). Virus DNA was electroporated into SW 105 cells and a second round of recombination was performed using specific oligonucleotides designed to delete (aa 4-22) within the ORF encoding HSV-1 gene UL20. Recombinant virus VC2 was recovered after transfection of Vero cells. Double deletions within the gK and UL20 genes were confirmed by capillary DNA sequencing. The absence of any other mutations within all HSV-1 structural proteins was confirmed by NGS sequencing using Ion Torrent Personal Genome Machine. Stocks of VC2, HSV-1 (McKrae), and HSV-2 (G), were grown to high titers and titrated in Vero cells.

Next Generation Genomic DNA Sequencing

DNA sequencing of the HSV-1 VC2 mutant virus was performed using the Ion Torrent Personal Genome Machine (PGM) and the 316 sequencing Chip (Life Technologies). Two independent total DNA samples derived from infected Vero cells and from partially purified virions were isolated using the PureLink Genomic DNA mini Kit (Invitrogen). The Ion Xpress Plus Fragment Library Kit (Life Technologies) was used to prepare high-quality fragment libraries from approximately 1 mg of total DNA. Template-positive Ion Sphere Particles (ISPs) containing clonally amplified DNA were produced using the Ion OneTouch 200 Template Kit v2 DL (for 200 base-read libraries) with the Ion OneTouch instrument. The Ion OneTouch ES instrument was used to enrich ISPs intended for the Ion PGM System using the Ion PGM 200 Sequencing Kit.

In-Vitro Characterization

Replication kinetics assay was performed on confluent monolayers of green African monkey kidney cells (Vero) in 12 well plates. Infections with either HSV-1 (F) or mutant virus VC2 were performed at an MOI of 0.1 and 5. Inoculated plates were placed at 4° C. for 1 hour to allow for virion attachment and returned to 37° C. for another hour to allow for entry. Plates were then washed with 1× Phosphate Buffered Saline and a final volume of 1 mL of complete DMEM 10% heat inactivated FBS applied to each. Plates were frozen at −80° C. until titrated for the following times post infection; 0, 2, 4, 6, 9, 12, 18, 24, and 36 hours. Samples were titrated on confluent monolayers of Vero cells. Infected cell cultures were fixed 48 hpi using formalin-acetic acid-alcohol (FAA) and stained with crystal violet. Plaques were counted using a light microscope and virion titers expressed as PFU/mL were derived for each sample.

Entry assay into CHO cells expressing known HSV-1 entry receptors was conducted as described in Chowdhury et al. (Chowdhury et al. (2013) J. Virol 87:3305-3313). Plaque morphology assays were conducted on confluent monolayers of Vero cells in 6-well formats. Virus was serial diluted until single isolated plaques were visible. Immunohistochemistry was performed using polyclonal rabbit anti-HSV-1 primary antibody (Dako, Denmark), polyclonal goat anti-rabbit immunoglobulins HRP conjugated secondary antibody (Dako, Denmark), and visualized using Vector® NovaRED Substrate Kit (Vector, Burlingame, Calif.). Substrate was allowed to develop until sufficient coloration for microscopic imagery.

Safety and Neurovirulence

Route of administration for neurovirulence assessment was conducted by inoculation of 20 mice with $10^6$ PFU either intranasally or intramuscularly, 10 in each group. Mice were monitored daily for 20 days post inoculation for the manifestation of disease. On day 21, mice were sacrificed and trigeminal ganglia for intranasal inoculations and dorsal root ganglia (for intramuscular inoculations) were collected. Total tissue DNA was extracted using the Qiagen DNeasy Blood and Tissue Kit (Qiagen) and viral genomes were estimated using quantitative PCR.

Vaccination

All animal studies were carried out after the appropriate approvals were obtained from the Louisiana State University Institutional Animal Care and Use Committee. Six week old female Balb/c mice (LSU DLAM Breeding Colony, Baton Rouge, La.) were used in this study. Each mouse was identified with an ear tag (National Band and Tag Company, KY, USA). Mice were divided into two groups to receive either the vaccine or mock inoculations. Eighty mice, 40 in each group, were mildly anesthetized by inhalation of 2-3% isoflurane and administered a single 100 uL intramuscular injection of either $1 \times 10^7$ PFU of VC-2 or equivalent volume of conditioned media. Mice were then observed daily collecting weight and clinical observations.

Tissue Collection and Analysis

On day 21 post vaccination 20 mice from each group were anesthetized by inhalation of 2-3% isoflurane and bled via cardiac stick. Maximum volume of blood was collected and mice were euthanized by cervical dislocation. Blood was allowed to clot at 4 C overnight in 5 mL falcon tubes (Becton Dickinson, Franklin lakes, NJ) and serum collected into 2 mL Sarstedt Screw Cap Micro Tubes (Sarstedt Inc, Newton, N.C.) and stored at −20 C until use. Spleens were excised from euthanized animals, minced and passed through a 10 um nylon mesh cell strainer (Fisher Scientific) in Hank's Balanced Salt Solution. Cell suspensions were then pelleted by centrifugation at 300×g for 5 minutes and frozen in 5% DMSO Heat Inactivated Fetal Bovine Serum at a concentration of $10^7$ cells/ml. Cells were stored in liquid nitrogen until use.

Dorsal root ganglia were excised as described in Murphy et al. (2000) J. Virol 74:7745-7754. Briefly, the peritoneal cavity of the mouse was opened and eviscerated of all organs. Tissues covering the ventral portion of the spine were removed. Dissection was conducted under magnification with a dissecting microscope. Carefully with curved scissors the spinal column was cut medially and scissors inserted into the subarachnoid space to make two lateral cuts along the length of the spine. Spinal cords were removed with attached dorsal root ganglia. DNA was extracted using the Qiagen DNeasy Blood and Tissue kit (Qiagen Sciences, Maryland, USA) as per the manufactures instructions and DNA was precipitated with an equal volume of isopropanol plus 0.3 M sodium acetate, washed with 70% ethanol, and resuspended to a final volume of 50 μL nuclease free water.

Polychromatic Flow Cytometry and Analysis

Cryopreserved Cells were resuspended at a concentration of $10^6$ cells/mL and labeled with the membrane stain Carboxyfluorescein succinimidyl ester (CFSE). Labeled cells were then cultured at a concentration of $10^5$ cells/well in a 96 well U-bottom plate and incubated at 37° C. and 5% $CO_2$ for 7 days in the presence of pooled peptides specific to either HSV-1 or HSV-2 at a concentration of 10 μg/mL Cells were then stained with polyclonal anti-mouse CD4 antibody conjugated to PE (BD Biosciences) and polyclonal anti-mouse CD8a antibody conjugated to APC (BD Biosciences). Proliferation of labeled T cell subsets was assessed using an Accuri C6 personal flow cytometer. Unstimulated CFSE-labeled spleenocytes were used to establish the $CFSE^{bright}$ population and to define the gating used to quantify $CFSE^{dim}$ (proliferating) T cells.

Supernatants from cultured spleenocytes were stored at −20 C until analysis. Cytokine responses from cultured spleenocytes were analyzed using the BD™ Cytometric Bead Array (CBA) Mouse Th1/Th2 Cytokine Kit (BD Biosciences, San Diego, Calif.) read using a Bioplex analyzer (Bio-Rad, Hercules, Calif.) as per the manufacturer's instructions.

Challenge

On day 15 post vaccination mice were administered Depo Provera (Upjohn, Kalamazoo, Mich.) via intra muscular injection as described previously Iyer et al. (Iyer et al. (2013) Virol. J. 10:317) On the day of challenge mice vaginas were swabbed with sterile polystyrene applicator tips dipped in 100 μL DMEM containing 50 mg/L primocin. $10^6$ plaque forming units of highly virulent HSV-1 (McKrae) or HSV-2 (G) were instilled in the vaginal vault and mice were closely monitored daily for clinical manifestation of disease recording daily weight and clinical scores. Mice were scored on a scale of 0-6 (0=no disease, 1=ruffled fur and generalized morbidity, 2=mild genital erythema and edema, 3=moderate genital inflammation, 4=genital inflammation with purulent discharge, 5=hind limb paralysis, 6=death). On the day an animal succumbed to disease, or on the day of sacrifice pertinent tissues were collected and preserved in 10% neutral buffered formalin (American Mastertech, Lodi, Calif.). Whole vaginas and brains were excised and submitted to histological staining. Unvaccinated challenged tissues were similarly collected and stained for the presence of virus at the time of death.

Latency Reactivation

Reactivation was conducted as described in Cook et al. (1991) Invest. Ophthalmol. Vis. Sci. 32:1558-1561. Briefly, on day 100 post challenge vaccinated mice, which had already survived challenge, received a series of intravenous injections. First 5 mg of cyclophosphamide (Baxter, Deerfield, Ill.) followed 24 hours later by 0.2 mg of dexamethasone (Butler Schein, Dublin, Ohio) injected via the same route. Mice were monitored daily for any clinical manifestation of disease. Vaginal swab samples were taken daily for 5 days prior to and post administration of cyclophosphamide and dexamethasone after which surviving mice were sacrificed for analysis of excised nervous tissue for the presence of viral DNA.

Quantitative PCR

Dorsal root ganglia (DRG) were resected from vaccinated mice and unvaccinated controls, challenged with either HSV1 McKrae or HSV2-G. The DRGs were vigorously aspirated and DNA was extracted using the Qiagen DNeasy Blood & Tissue Kit™ as per the manufacturer's instructions. The eluted DNA was quantified using a Nanodrop 1000™ spectrophotometer. Equal amounts of DNA from each sample were used to perform quantitative real-time PCR analysis on an Applied Biosystems 7900HT Fast Real-Time PCR System. Viral DNA from purified HSV-1 (McKrae) and HSV-2(G) were used as positive controls. The following primer/probe combinations were used to specifically detect HSV-1 (McKrae) or HSV-2(G) (see also Table 1):

```
(1) HSV1gDFP
                                    (SEQ ID NO: 20)
ACGTACCTGCGGCTCGTGAAGA (2) HSV1 Probe
                                    (SEQ ID NO: 21)
Fam-AGCCAAGGGCTCCTGTAAGTACGCCCT-Tamra (3) HSV1 gD RP
                                    (SEQ ID NO: 22)
TCACCCCCTGCTGGTAGGCC (4) HSV2gDFP
                                    (SEQ ID NO: 23)
CCGCGGGTACGTACCTGCGGCTAG (5) HSV2 Probe
                                    (SEQ ID NO: 24)
HEX-GGCCC GCGC/ZEN/CTCCTGCAAGTACGCTCT-IABkFQ
and (6) HSV2 gD RP
                                    (SEQ ID NO: 25)
GCCCTGTTGGTAGGCCTTCGAGGTG.
```

To determine the sensitivity of the qPCR assay, HSV-1 and HSV-2 genomic DNA were quantified and their respective molar concentrations was calculated using the formula:— {µg DNA×(pmol/660)×($10^6$ pg/1 µg)×(1/N)=pmol DNA, where N=number of nucleotides}. Ten-fold serial dilutions ranging from $10^5$-$10^{0.1}$ molecules were used as template samples in Taqman PCR reactions, and water was used a no template control. qPCR was performed on the Applied biosystems 7900HT Fast Real-Time PCR System. HSV target DNA was detected at the lowest dilution ($2.7 \times 10^{-8}$ µg of DNA) containing 3 copies per µL. No viral DNA was detected in the no template control sample. The linear range of detection ranged from 3 to $10^6$ viral DNA copies with mock-vaccinated mice exhibiting more than $10^6$ viral DNA copies per sample.

Virus Shedding

On the day of challenge, before administration of virus, and daily following inoculation, vaginas were swabbed with sterile polystyrene applicator tips dipped in 100 µL DMEM containing 50 mg/L Primocin (InvivoGen, San Diego, Calif.). Swab samples were stored at −80° C. until titration. Titration of swab samples was conducted on confluent monolayers of Vero cells. Samples were resuspended in 900 µL of DMEM+50 mg/L Primocin for an initial dilution of $10^{-1}$ and diluted in 10 fold increments out to 10'. 250 µL of each dilution was plated in duplicate and incubated at 24° C. for 1 hour. Dilutions were then aspirated and wells were covered with 1% DMEM methylcellulose containing 1% FBS and 50 mg/L Primocin. Plates were then incubated at 37° C. with 5% $CO_2$ for 36-48 hours until visible plaques had formed. Plates were then fixed with FAA and stained with crystal violet. Plaques were counted at dilutions yielding greater than 20 plaques per well.

Antibody ELISA and Serum Neutralization

Relative anti-HSV-1 IgG serum concentrations were quantified using commercially available Mouse/Rat HSV-1 IgG ELISA (Calbiotech, Spring Valley, Calif.). Serum collected on day 21 was used to neutralize 50 µL of stock HSV-1 McKrae and HSV-2 G. Serum was first diluted 1:10 in complete DMEM containing 10% heat inactivated FBS. Diluted serum was then two fold serial diluted to 1:160. 50 µL of stock virus was then added to each dilution of serum, 50 µL each, to a total volume of 100 µL. Addition of virus made serum dilutions 1:20, 1:40, 1:80, 1:160, and 1:320. Serum virus mixtures were then placed on a rocker at room temperature for 1 hour and frozen at −80 C until titration on Vero cells.

Example 2: The gKΔ31-68 Mutation Prevents HSV Entry in Neuronal Axons

Figure 9:
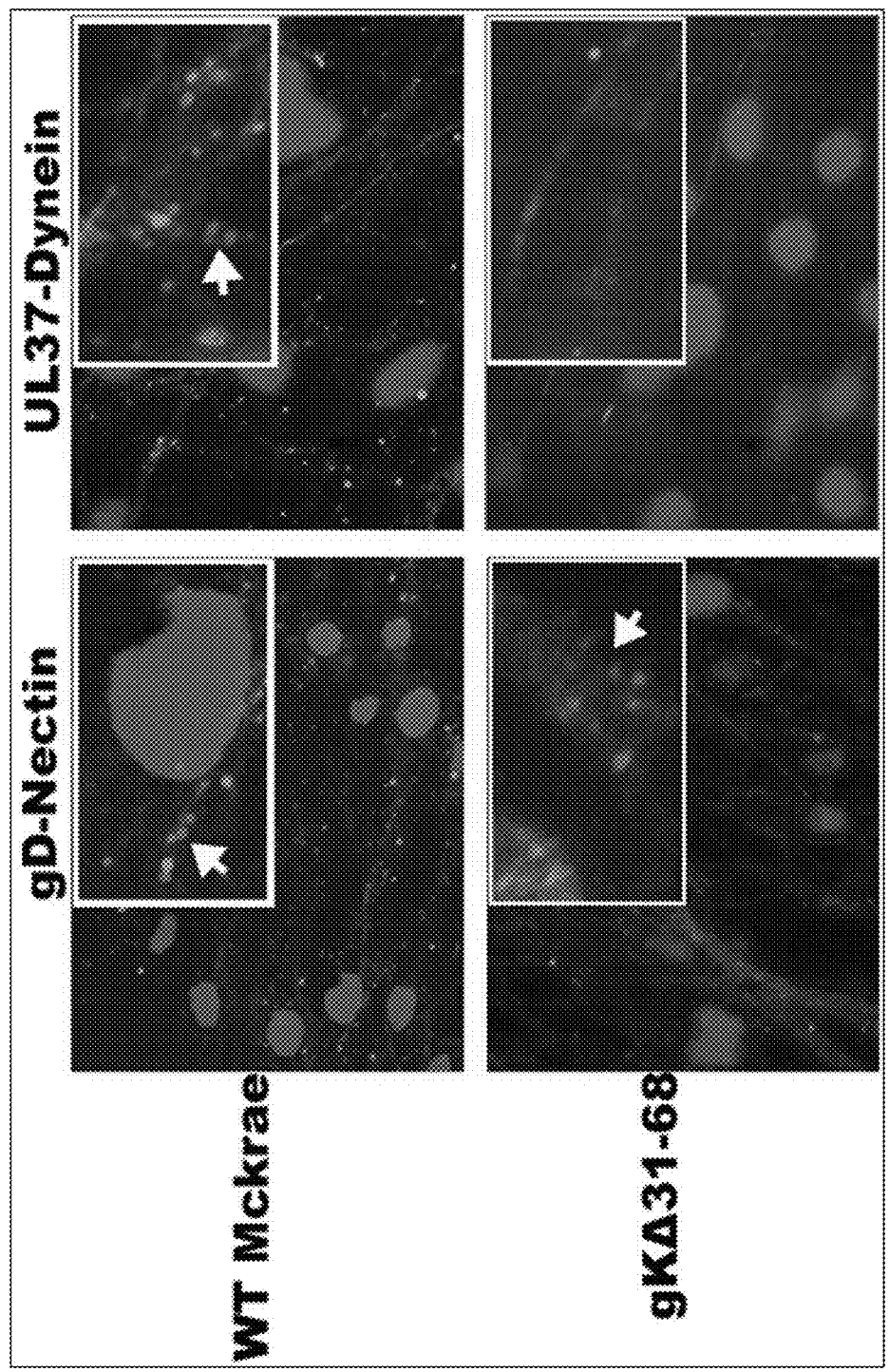
FIG. 9. Proximity ligation assay (PLA) for virus binding and virus entry and cell-to-cell fusion. Primary mouse cortical neurons were infected with HSV-1 McKrae or HSV-1 McKraegKΔ31-68 at an MOI of 5. PLA was performed at 0 hours post infection with anti-gD and antin-nectin-1 mAbs to detect cell-surface bound virus after absorption of the virus for 2 hours at 4° C. (top and bottom left panels) and with anti-dynein and anti-UL37 antibody after 1 hour incubation at 37° C., respectively (top and bottom right panels).

Recently, a novel assay was developed for the assessment of virion entry into cytoplasm of cells by adapting the proximity ligation assay (PLA) (Jarvius et al. (2007) *Mol. Cell. Proteomics* 6:1500-1509; Soderberg et al. (2006) *Nat. Methods* 3:995-1000; Soderberg et al. (2008) Methods 45:227-232). PLA has been extensively utilized to determine whether two different proteins colocalize and likely interact in the cytoplasm of cells. PLA is performed by first attaching specific antibodies to the two proteins of interest, and then attaching to these primary antibodies two secondary antibodies covalently linked with a short DNA primer. When the two primers are in close proximity to each other, they can interact with two other circle-forming primers that are added later. Enzymatic ligation of these two fluorescently-labeled oligonucleotides followed by polymerase-dependent rolling circle amplification result in the generation of intense fluorescence visualized as a distinct bright spot using a fluorescence microscope (Jarvius et al. (2007) *Mol. Cell. Proteomics* 6:1500-1509; Soderberg et al. (2006) *Nat. Methods* 3:995-1000). PLA was utilized to detect the known gD/Nectin-1 interactions on infected cell surfaces immediately after a 2 hour adsorption of the virus at 4° C. on ganglionic neurons, when the virus was attached to cell surfaces, but not yet entered into cells (FIG. 9). To determine cytoplasmic entry we specifically targeted the UL37 tegument protein and dynein, since published literature has suggested that UL37/UL36 protein complex interacts with the dynein motor complex. PLA using anti-UL37 and anti-dynein antibodies detected UL37 colocalization with dynein in the cytoplasm after incubation of the infected cells at 37° C. for one hour (FIG. 9). This assay effectively demonstrates that HSV-1 (McKrae) gKΔ31-68 attached efficiently, but was defective for entry into neuronal axons.

The article "a" and "an" are used herein to refer to one or more than one (i.e., to at least one) of the grammatical object of the article. By way of example, "an element" means one or more element.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

---

That which is claimed:

1. A vaccine for treating or preventing a herpes simplex virus (HSV) infection, the vaccine comprising a recombinant HSV, wherein the recombinant HSV comprises a recombinant HSV genome comprising:

(a) a modified UL53 gene comprising a deletion corresponding to the region of the UL53 gene that encodes amino acids 31-68 of wild-type gK; and (b) a modified UL20 gene comprising a deletion corresponding to the region of the UL20 gene that encodes amino acids 4-22 of wild-type UL20 protein;

wherein the recombinant HSV is capable of replication in a host cell and incapable of entry into axonal compartments of neurons.

2. The vaccine of claim 1, wherein the recombinant HSV genome is derived from the genome of HSV-1 or HSV-2.

3. The vaccine of claim 2, wherein HSV-1 is HSV-1 strain F.

4. The vaccine of claim 1, wherein the genome comprises a member selected from the group consisting of:
   (a) the nucleotide sequence set forth in SEQ ID NO: 5;
   (b) a nucleotide sequence comprising at least 90% identity to the nucleotide sequence set forth in SEQ ID NO: 5;
   (c) a nucleotide sequence encoding the amino acid sequence set forth in SEQ ID NO: 6;
   (d) a nucleotide sequence encoding an amino acid sequence comprising at least 90% identity to the amino acid sequence set forth in SEQ ID NO: 6;
   (e) the nucleotide sequence set forth in SEQ ID NO: 7;
   (f) a nucleotide sequence comprising at least 90% identity to the nucleotide sequence set forth in SEQ ID NO: 7;
   (g) a nucleotide sequence encoding the amino acid sequence set forth in SEQ ID NO: 8;
   (h) a nucleotide sequence encoding an amino acid sequence comprising at least 90% identity to the amino acid sequence set forth in SEQ ID NO: 8; and
   (i) the nucleotide sequence of (a), (b), (c), or (d) and the nucleotide sequence of (e), (f), (g), or (h).

5. The vaccine of claim 1, wherein the recombinant HSV is a live virus.

6. The vaccine of claim 1, wherein the HSV infection comprises a genital HSV infection.

7. The vaccine of claim 1, wherein the HSV infection comprises or further comprises an orofacial HSV infection.

8. The vaccine of claim 1, further comprising a pharmaceutically acceptable component selected from the group consisting of a carrier, an excipient, a stabilizing agent, a preservative, an immunostimulant, and an adjuvant.

9. A method of immunizing a patient against an HSV infection comprising the step of administering to the patient a therapeutically effective amount of the vaccine of claim 1.

10. An recombinant herpes simplex virus (HSV) genome comprising:
   (a) a modified UL53 gene comprising a deletion corresponding to the region of the UL53 gene that encodes amino acids 31-68 of wild-type gK; and
   (b) a modified UL20 gene comprising a deletion corresponding to the region of the UL20 gene that encodes amino acids 4-22 of wild-type UL20 protein;
wherein a virus comprising the genome is capable of replication in a host cell and incapable of entry into axonal compartments of neurons.

11. An immunogenic composition or virus comprising the recombinant HSV genome of claim 10.

12. A method for producing a vaccine or immunogenic composition, the method comprising:
   (a) transfecting a host cell with the recombinant HSV genome of claim 10;
   (b) incubating the transfected host cell under conditions favorable for the formation of a recombinant HSV virus comprising the recombinant HSV genome;
   (c) purifying the recombinant HSV virus comprising the recombinant HSV genome; and optionally
   (d) combining the purified recombinant HSV virus with at least one pharmaceutically acceptable component.

13. A method for producing a recombinant HSV, the method comprising:
   (a) transfecting a host cell with the recombinant HSV genome of claim 10; and
   (b) incubating the transfected host cell under conditions favorable for the formation of a recombinant HSV virus comprising the recombinant HSV genome, whereby a recombinant HSV is produced.

* * * * *